(12) United States Patent
Kuroita et al.

(10) Patent No.: US 7,422,882 B2
(45) Date of Patent: Sep. 9, 2008

(54) MODIFIED THERMOSTABLE DNA POLYMERASE

(75) Inventors: Toshihiro Kuroita, Tsuruga (JP); Masao Kitabayashi, Tsuruga (JP); Yoshikazu Ishida, Tsuruga (JP); Hideyuki Komatsubara, Tsuruga (JP); Yoshiaki Nishiya, Tsuruga (JP); Bunsei Kawakami, Tsuruga (JP); Yoshihisa Kawamura, Tsuruga (JP); Tadayuki Imanaka, Suita (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 09/852,922

(22) Filed: May 10, 2001

(65) Prior Publication Data

US 2002/0076768 A1  Jun. 20, 2002

(30) Foreign Application Priority Data

May 11, 2000  (JP)  .............................. 2000-138796

(51) Int. Cl.
C12N 9/12  (2006.01)
C12P 19/34  (2006.01)
(52) U.S. Cl. ........................ 435/194; 435/183; 435/91.1
(58) Field of Classification Search ................. 435/194, 435/103, 91.1, 69.1, 440; 530/23.1, 23.2, 530/23.7
See application file for complete search history.

(56) References Cited

FOREIGN PATENT DOCUMENTS

| EP | 0 745 675 A | 12/1996 |
|---|---|---|
| EP | 0 822 256 A | 2/1998 |
| EP | 0 547 359 B1 | 3/2002 |
| JP | 05-328969 | 12/1993 |
| JP | 06-007160 | 1/1994 |
| JP | 7-298879 | 11/1995 |
| JP | 07-298879 | 11/1995 |
| JP | 10-042871 | 2/1998 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*
L. Blanco et al., *A general structure for DNA-dependent DNA polymerases*, Gene 100, 27-38 (1991).
L. Blanco et al., *Evidence favouring the hypothesis of a conserved 3'-5' exonuclease active site in DNA-dependent DNA polymerases*, Gene 112, 139-144 (1992).
H. Kong et al., *Characterization of a DNA Polymerase from the Hyperthermophile Archaea Thermococcus litoralis*, The Journal of Biological Chemistry 268(3), 1965-1975 (1993).
Fujii et al., *DNA Replication Errors Produced by the Replicative Apparatus of Escherichia coli*, Journal of Molecular Biology 289, 835-850 (1999).
S. Tabor et al., *Selective Inactivation of the Exonuclease Activity of Bacteriophage T7 DNA Polymerase by in Vitro Mutagenesis*, The Journal of Biological Chemistry 264 (11), 6447-6458 (1989).
T. Uemori et al., *Orangization and nucleotide sequence of the DNA polymerase gene from the archaeon Pyrococcus furiosus*, Nucleic Acids Research 21(2), 259-265 (1993).
F. B. Perler et al., *Intervening sequences in an Archaea DNA polymerase gene*, Proc. Natl. Acad. Sci. USA 89, 5577-5581 (1992).
R. K. Saiki et al., *Analysis of enzymatically amplified β-globin and HLA-DQα DNA with allele-specific oligonucleotide probes*, Nature 324, 163-166 (1986).
W. M. Barnes, *PCR amplification of up to 35-kb DNA with high fidelity and high yield from λ bacteriophage templates*, Proc. Natl. Acad. Sic. USA 91, 2216-2220 (1994).
*Preparation and Transformation of Competent E. coli*, Molecular Cloning, 2nd Edition, 1.74-1.81.
M. W. Southworth et al., *Cloning of thermostable DNA polymerases from hyperthermophilic marine Archaea with emphasis on Thermococcus sp. 9 degree N-7 and mutations affecting 3'-5' exonuclease activitiy*, Proceedings of the National Academy of Sciences of the United States 93(11), 5281-5285 (1996).
F.C. Lawyer, et al., *High-Level Expression, Purification, and Enzymatic Characterization of Full-Length Thermus Aquaticus DNA Polymerase and a Truncated Form Deficient in 5' to 3' Exonuclease Activity*, PCR Methods & Applications, Cold Spring Harbor Laboratory Press, US 2, 275-287 (1993).
Ruepp et al., *DNA polymerase related protein*, Database Genbank Online, Accession# AL445064, Oct. 4, 2000 (abstract) ).
T. Uemori et al., *The hyperthermophilic archaeon Pyrodictium ocultum has two alpha-like DNA polymerase*, Journal of Bacteriology 177(8), 2164-2177 (1995).
Crystal Structure of DNA Polymerase from Hyperthermophilic Archaeon *Pyrococcus kodakaraensis* KOD1, Hiroshi Hashimoto et al., J. Mol. Biol. (2001) 306, 469-477.
Crystal Structure of a Pol α Family DNA Polymerase from the Hyperthermophilic Archaeon Thermococcus sp. 9•N-7, A. Chapin Rodrigueq et al., J. Mol. Biol. (2000) 299-447-462.
Crystal structure of a thermostable type B DNA polymerase from *Thermococcus gorgonarius*, Karl-Peter Hopfner et al., Proc. Natl. Acad. Sci. USA, vol. 96, pp. 3600-3605, Mar. 1999, Biochemistry.
Structural Mechanism for Coordination of Proofreading and Polymerase Activities in Archaeal DNA Polymerases, Toshihiro Kuroita et al., J. Mol. Biol. (2005) 351, 291-298.
Organization and nucleotide sequence of the DNA polymerase gene from the archaeon *Pyrococcus furiosus*, Takashi Uemori et al., 1993 Oxford University Press, Nucleic Acids Research, 1993, vol. 21. No. 2, 259-265.

* cited by examiner

*Primary Examiner*—Richard G Hutson
(74) *Attorney, Agent, or Firm*—Kenyon & Kenyon LLP

(57) ABSTRACT

An object of the present invention is to provide a thermostable DNA polymerase with enhanced amplification efficiency and/or improved fidelity in polymerase chain reaction (PCR), and provide a process for production thereof. More specifically, the present invention provides thermostable DNA polymerase wherein in the $DX_1EX_2X_3X_4H$ sequence (D: aspartic acid, E: glutamic acid, H: histidine, $X_1$, $X_2$, $X_3$ and $X_4$: any amino acid) consisting of $DX_1E$ sequence within the EXO I region and a four amino acid length peptide adjacent to said glutamic acid(E) of thermostable DNA polymerase having 3'-5' exonuclease activity, histidine(H) has been replaced by another amino acid.

25 Claims, 3 Drawing Sheets

| | | |
|---|---|---|
| Archaeon-derived | KOD(Pyrococcus) | : MLAFDIETLYHEG |
| | Pfu(Pyrococcus) | : ILAFDIETLYHEG |
| | Vent(Thermococcus) | : LLAFDIETFYHEG |
| | Sso(Sulfolobus) | : RVAIDIEVYTPVK |
| Phage-derived | T7 | : MIVSDIEANALLE |
| | T4 | : VANCDIEVTGDKF |

MODIFIED THERMOSTABLE DNA POLYMERASE

TECHNICAL FIELD

The present invention relates to a thermostable DNA polymerase with enhanced amplification efficiency and/or improved fidelity in polymerase chain reaction (PCR), and to a process for production thereof. The present invention further relates to a method for amplifying nucleic acid using the thermostable DNA polymerase, and a reagent kit comprising the thermostable DNA polymerase.

In resent years, PCR has been one of the essential techniques for research and testing in the fields of biochemistry, molecular biology and clinicopathology. A feature of PCR is that the reaction is carried out using a thermostable DNA polymerase. The DNA polymerases most frequently utilized currently are, mainly, thermostable DNA polymerases called "Pol I-like", such as a thermostable DNA polymerase derived from *Thermus aquaticus* (Taq DNA polymerase) and a thermostable DNA polymerase derived from *Thermus thermophilus* (Tth DNA polymerase). The advantageous characteristics of Pol I-like DNA polymerases are high amplification efficiency and easiness to set conditions. However, these enzymes have a defect of low fidelity in nucleic acid incorporation during amplification and are considered to be unsuitable for use in the case of cloning the amplified DNA.

Other known polymerases are "α-like" DNA polymerases derived from *hyperthermophilic archaea,* such as a thermostable DNA polymerase derived from *Pyrococcus furiosus* (Pfu DNA polymerase, WO92/09689, Japanese Unexamined Patent Publication No. 1993-328969), a thermostable DNA polymerase derived from *Thermococcus litoralis* (Ti(Vent) polymerase, Japanese Unexamined Patent Publication No. 1994-7160), and a thermostable DNA polymerase derived from *Pyrococcus kodakaraensis* KOD1 (former name: Pyrococcus sp. KOD1)(KOD DNA polymerase, Japanese Unexamined Patent Publication No. 1995-298879). Advantageous characteristics of α-like DNA polymerases are that the polymerases have 3'-5' exonuclease activity (proof-reading activity) and high fidelity in nucleic acid incorporation as compared with Pol I-like DNA polymerases such as Taq DNA polymerase.

However, α-like DNA polymerases have problems such as insufficient PCR amplification efficiency. Furthermore, most of the α-like DNA polymerases have the disadvantage that optimal conditions for PCR such as reaction time, enzyme amount and primer concentration are limited to narrow ranges.

The 3'-5' exonuclease activity level is presumably a cause of the aforementioned problems with PCR amplification using α-like DNA polymerase. Stated more specifically, it is considered that nucleotides are removed from primers etc. by 3'-5' exonuclease activity during PCR, whereby PCR amplification efficiency is reduced. Further, since α-like DNA polymerase has a 3'-5' exonuclease activity domain and a DNA polymerase activity domain in a single protein, it is presumed that the interaction between the two activities and the difference between these sites in affinity to nucleic acid also affect PCR amplification.

It is known that highly conserved amino acid regions (EXO I (FIG. 1), EXO II and EXO III) of α-like DNA polymerase might play a significant role in expressing 3'-5' exonuclease activity (*Gene,* 100, 27-38 (1991), *Gene,* 112, 139-144 (1992)). It is known that XDXEX sequence (D: aspartic acid, E: glutamic acid, each of X: any amino acid) exists in the EXO I region, and aspartic acid (D) and glutamic acid (E) are essential for exhibiting exonuclease activity (Kong, et al. (1993), *Journal of Biological Chemistry,* vol. 268, 1965-1975). According to the above publication, exonuclease activity can be reduced to 1/10000 or less by replacement of aspartic acid and glutamic acid in the EXO I region by alanine which is a neutral amino acid. However, there exists a problem that when exonuclease activity is reduced to 1/10000 or less, high fidelity of DNA replication, which is an advantageous characteristic of α-like DNA polymerases, is also lost simultaneously.

Further, there is a report on an attempt to gradually reduce 3'-5' exonuclease activity by replacing an amino acid represented by $X_1$ in the above $X_0DX_1EX_2$ sequence of KOD DNA polymerase with a different amino acid (Japanese Unexamined Patent Publication No. 1998-42871). According to the method disclosed therein, as 3'-5' exonuclease activity decreases, enhanced PCR efficiency and reduced amplification fidelity are observed simultaneously. Therefore, in the case of replacing the above-mentioned amino acid ($X_1$), it is important to prepare a modified enzyme whose 3'-5' exonuclease activity has been reduced within the range that fidelity of enzyme amplification is not impaired. However, enzymes produced according to the above method, such as variants IQ and IK prepared by replacing isoleucine(I) at the 142-position from the 5'-terminal of KOD DNA polymerase by glutamine (Q) and lysine(K) respectively, do not always show high amplification efficiency from low copy number of template DNA and therefore, can not be regarded as variants achieving high PCR efficiency (FIG. 3).

According to Japanese Unexamined Patent Publication No. 1998-42871, it is difficult to produce mutants with enhanced 3'-5' exonuclease activity (proof-reading activity) by the method disclosed therein.

The present inventors produced various mutants of KOD DNA polymerase and carried out extensive research to solve the above problems. The present inventors found that when the histidine residue that is the fourth amino acid from glutamic acid(E) of $X_0DX_1EX_2$ sequence in the EXO I region (i.e., at the 147-position; hereinafter sometimes referred to as "H") is replaced by various amino acids, there can be produced thermostable DNA polymerases with different levels of 3'-5' exonuclease activity, PCR efficiency and fidelity. Based on this finding, the present invention has been accomplished (the motif including this histidine is hereinafter referred to as $DX_1EX_2X_3X_4H$ sequence).

The present invention includes the following subject matters:

1. A modified thermostable DNA polymerase wherein in the $DX_1EX_2X_3X_4H$ sequence (D: aspartic acid, E: glutamic acid, H: histidine, $X_1$, $X_2$, $X_3$ and $X_4$: any amino acid) consisting of $DX_1E$ sequence within the EXO I region and a four amino acid length peptide adjacent to said glutamic acid(E) of thermostable DNA polymerase having 3'-5' exonuclease activity, histidine(H) has been replaced by another amino acid.

2. The modified thermostable DNA polymerase according to item 1, wherein in the $DX_1EX_2X_3X_4H$ sequence, histidine (H) has been replaced by an amino acid selected from the group consisting of aspartic acid, glutamic acid, tyrosine, alanine, lysine and arginine.

3. The modified thermostable DNA polymerase according to item 1 having the following physicochemical properties:
   (1) DNA extension rate: at least 20 bases/second; and
   (2) thermostability: it is capable of retaining 10% or more DNA polymerase activity of untreated DNA polymerase at pH 8.8 (determined at 25° C.) after treatment at 95° C. for 6 hours.

4. The modified thermostable DNA polymerase according to item 3 having the following physicochemical properties:
   (1) DNA extension rate: at least 30 bases/second;
   (2) thermostability: it is capable of retaining 40% or more DNA polymerase activity of untreated DNA polymerase at pH 8.8 (determined at 25° C.) after treatment at 95° C. for 6 hours; and
   (3) amino acid sequence: in the DIETLYH sequence (SEQ ID NO:35) (D: aspartic acid, I: isoleucine, E: glutamic acid, T: threonine, L: leucine, Y: tyrosine, H: histidine) located at the 141- to 147-positions in the amino acid sequence of SEQ ID NO: 2, histidine(H) has been replaced by another amino acid.

5. The modified thermostable DNA polymerase according to item 4 having the following physicochemical properties:
   (1) DNA extension rate: at least 30 bases/second;
   (2) thermostability: it is capable of retaining 60% or more DNA polymerase activity of untreated DNA polymerase at pH 8.8 (determined at 25° C.) after treatment at 95° C. for 6 hours; and
   (3) amino acid sequence: in the DIETLYH sequence (SEQ ID NO:35) (D: aspartic acid, I: isoleucine, E: glutamic acid, T: threonine, L: leucine, Y: tyrosine, H: histidine) located at the 141- to 147-positions in the amino acid sequence of SEQ ID NO: 2, histidine(H) has been replaced by another amino acid.

6. The modified thermostable DNA polymerase according to item 5, wherein in the amino acid sequence of SEQ ID NO: 2, histidine(H) at the 147-position has been replaced by an amino acid selected from the group consisting of aspartic acid, glutamic acid, tyrosine, alanine, lysine and arginine.

7. The modified thermostable DNA polymerase according to item 6, wherein in the amino acid sequence of SEQ ID NO: 2, histidine(H) at the 147-position has been replaced by aspartic acid.

8. The modified thermostable DNA polymerase according to item 6, wherein in the amino acid sequence of SEQ ID NO: 2, histidine(H) at the 147-position has been replaced by glutamic acid.

9. The modified thermostable DNA polymerase according to item 6, wherein in the amino acid sequence of SEQ ID NO: 2, histidine(H) at the 147-position has been replaced by tyrosine.

10. The modified thermostable DNA polymerase according to item 6, wherein in the amino acid sequence of SEQ ID NO: 2, histidine(H) at the 147-position has been replaced by alanine.

11. The modified thermostable DNA polymerase according to item 6, wherein in the amino acid sequence of SEQ ID NO: 2, histidine (H) at the 147-position has been replaced by lysine.

12. The modified thermostable DNA polymerase according to item 6, wherein in the amino acid sequence of SEQ ID NO: 2, histidine(H) at the 147-position has been replaced by arginine.

13. A gene encoding a modified thermostable DNA polymerase wherein in the $DX_1EX_2X_3X_4H$ sequence (D: aspartic acid, E: glutamic acid, R: histidine, $X_1$, $X_2$, $X_3$ and $X_4$: any amino acid) consisting of $DX_1E$ sequence within the EXO I region and four amino acid length peptide adjacent to said glutamic acid(E) of thermostable DNA polymerase having 3'-5' exonuclease activity, histidine(H) has been replaced by another amino acid.

14. The gene according to item 13 which encodes a modified thermostable DNA polymerase having the following physicochemical properties:
   (1) DNA extension rate: at least 20 bases/second; and
   (2) thermostability: it is capable of retaining 10% or more DNA polymerase activity of untreated DNA polymerase at pH 8.8 (determined at 25° C.) after treatment at 95° C. for 6 hours.

15. The gene according to item 13 which encodes a modified thermostable DNA polymerase having the following physicochemical properties:
   (1) DNA extension rate: at least 30 bases/second;
   (2) thermostability: it is capable of retaining 40% or more DNA polymerase activity of untreated DNA polymerase at pH 8.8 (determined at 25° C.) after treatment at 95° C. for 6 hours; and
   (3) amino acid sequence: in the DIETLYH sequence (SEQ ID NO:35) (D: aspartic acid, I: isoleucine, E: glutamic acid, T: threonine, L: leucine, Y: tyrosine, H: histidine) located at the 141- to 147-positions in the amino acid sequence of SEQ ID NO: 2, histidine(H) has been replaced by another amino acid.

16. The gene according to item 13 which encodes a modified thermostable DNA polymerase having the following physicochemical properties:
   (1) DNA extension rate: at least 30 bases/second;
   (2) thermostability: it is capable of retaining 60% or more DNA polymerase activity of untreated DNA polymerase at pH 8.8 (determined at 25° C.) after treatment at 95° C. for 6 hours; and
   (3) amino acid sequence: in the DIETLYH sequence (SEQ ID NO:35) (D: aspartic acid, I: isoleucine, E: glutamic acid, T: threonine, L: leucine, Y: tyrosine, H: histidine) located at the 141- to 147-positions in the amino acid sequence of SEQ ID NO: 2, histidine(H) has been replaced by another amino acid.

17. A recombinant DNA vector obtained by inserting the gene of any one of items 13 to 16 into an expression vector.

18. The recombinant DNA vector according to item 17, wherein the expression vector is pLED-MI, pBluescript or their derivatives.

19. A transformant produced by transforming a host cell with the recombinant DNA vector of item 17 or 18.

20. The transformant according to item 19 wherein the host cell is *Escherichia coli*.

21. A process for producing a modified thermostable DNA polymerase, which comprises culturing the transformant of item 20 and recovering the thermostable DNA polymerase from the culture broth.

22. A method for amplifying or extending nucleic acid, which comprises reacting DNA as a template, one or more kinds of primers, dNTP and the thermostable DNA polymerase of any one of items 1 to 12, thus extending the primer(s) to synthesize DNA primer extension product(s).

23. The method for amplifying nucleic acid according to item 22, wherein the primers are 2 kinds of oligonucleotides, each of the primers being complementary to a DNA extension product of the other primer.

24. The method for amplifying nucleic acid according to item 22, which comprises heating and cooling repeatedly.

25. A reagent kit for amplifying nucleic acid, which comprises 2 kinds of primers, each of the primers being complementary to a DNA extension product of the other primer; dNTP; the thermostable DNA polymerase of any one of items 1-12; divalent ion(s); monovalent ion(s); and a buffer solution.

26. A reagent kit for amplifying nucleic acid, which comprises 2 kinds of primers, each of the primers being complementary to a DNA extension product of the other primer; dNTP; the thermostable DNA polymerase of any one of items 1-12; magnesium ion; at least one of monovalent ions selected from the group consisting of ammonium ion and potassium ion; BSA (bovine serum albumin); a nonionic surfactant and a buffer solution.

27. A reagent kit for amplifying nucleic acid, which comprises 2 kinds of primers, each of the primers being complementary to a DNA extension product of the other primer; dNTP; the thermostable DNA polymerase of any one of items 1-12; magnesium ion; at least one of monovalent ions selected from the group consisting of ammonium ion and potassium ion; BSA (bovine serum albumin); a nonionic surfactant; a buffer solution and an antibody capable of suppressing at least one activity selected from polymerase activity and 3'-5' exonuclease activity of the thermostable DNA polymerase.

28. A DNA polymerase composition which comprises one or more kinds of modified thermostable DNA polymerases defined in any of items 1-12.

29. A method of producing a mutated DNA which comprises reacting DNA as a template, mutagenesis primers, dNTP and the thermostable DNA polymerase of any one of items 1 to 12, thus extending the primers to synthesize DNA primer extension products.

30. A reagent kit for producing a mutated DNA which comprises mutagenesis primers, dNTP and the thermostable DNA polymerase of any one of items 1 to 12.

DNA Polymerase Activity

In the present invention, "DNA polymerase activity" refers to a catalytic activity to template-dependently introduce deoxyribonucleoside-5'-monophosphate into deoxyribonucleic acid by covalently binding α-phosphate of deoxyribonucleoside-5'-triphosphate to the 3'-hydroxyl group of an oligonucleotide or polynucleotide annealed to a template DNA.

If the enzyme activity in a sample is high, activity measurement shall be carried out after the sample is diluted with a storage buffer (for example, 50 mM Tris-HCl(pH8.0), 50 mM KCl, 1 mM DTT, 0.1% Tween 20, 0.1% Nonidet P40, 50% glycerin). In the present invention, 25 μl of Solution A shown below, 5 μl each of Solutions B and C shown below, 10 μl of sterilized water and 5 μl of an enzyme solution are pipetted into a microtube and reacted at 75° C. for 10 minutes. Thereafter, the sample is cooled on ice, and 50 μl of Solution E and 100 μl of Solution D shown below are added and stirred, followed by cooling with ice for 10 minutes. The solution is filtered through a glass filter (Wattman GF/C Filter), and the filter is washed intensively with Solution D and ethanol, and the radioactivity of the filter is counted in a liquid scintillation counter (Packard) to determine the incorporation of the nucleotide into the template DNA. 1 unit of enzyme activity is defined as the amount of the enzyme that catalyzes an incorporation of 10 nmole of total nucleotides into the acid-insoluble fraction (i.e., DNA fraction which becomes insoluble when Solution D is added) per 30 minutes under the above conditions.

Solution A: 40 mM Tris-HCl buffer (pH 7.5)
  16 mM magnesium chloride
  15 mM dithiothreitol
  100 μg/ml BSA
Solution B: 2 μg/μl activated calf thymus DNA
Solution C: 1.5 mM dNTP (250 cpm/pmol [$^3$H]dTTP)
Solution D: 20% trichloroacetic acid (2 mM sodium pyrophosphate)
Solution E: 1 mg/ml salmon sperm DNA 3'-5' Exonuclease Activity In the present invention, "3'-5' exonuclease activity" refers to the activity of deleting a 3'-terminal region of DNA to release 5'-mononucleotide. The activity measurement method is as follows: 50 μl reaction solution (120 mM Tris-HCl (pH 8.8 at 25° C.), 10 mM KCl, 6 mM ammonium sulfate, 1 mM MgCl$_2$, 0.1% Triton X-100, 0.001% BSA and 5 μg of E. coli DNA labeled with tritium) are pipetted into a 1.5 ml microtube, followed by addition of DNA polymerase. The mixture is reacted at 75° C. for 10 minutes and then cooled with ice to terminate the reaction. After 50 μl of 0.1% BSA is added as a carrier to the reaction mixture, 100 μl of a solution containing 10% trichloroacetic acid and 2% sodium pyrophosphate is added and mixed. The mixture is left on ice for 15 minutes and then centrifuged at 12,000 r.p.m. (rotations per minute) for 10 minutes to separate a supernatant from the precipitate. 100 μl of the supernatant is measured for radioactivity in a liquid scintillation counter (Packard) to determine the amount of the nucleotide delivered to the acid soluble fraction.

DNA Extension Rate

In the present invention, "DNA extension rate" refers to the number of extended nucleotides per one second (bases/second) on an elongation reaction of DNA polymerase. The measurement method is as follows: A reaction solution of DNA polymerase (20 mM Tris-HCl (pH 7.5), 8 mM magnesium chloride, 7.5 mM dithiothreitol, 100 μg/ml BSA, 0.1 mM dNTP, 0.2 μCi [α-$^{32}$P]dCTP) is reacted at 75° C. with single-stranded M13mp18 DNA to which a primer had been annealed. The reaction is terminated by adding an equal volume (equal to the reaction mixture) of a reaction terminating solution (50 mM sodium hydroxide, 10 mM EDTA, 5% Ficoll, 0.05% Bromophenol Blue). The DNA fragments are sized by electrophoresis on an alkaline agarose gel, and the gel is dried and subjected to autoradiography. As the DNA size marker, labeled λ/HindIII is used. DNA extension rate is determined by measuring the extended DNA size using a band of this marker as an indicator.

Thermostability (Residual Polymerase Activity After Heat Treatment)

In the present invention, "thermostability" means residual activity after mixing 5 units of DNA polymerase with 100 μl of a buffer (20 mM Tris-HCl (pH 8.8, the pH value determined at 25° C.), 10 mM potassium chloride, 10 mM ammonium sulfate, 2 mM magnesium sulfate, 0.1% Triton X-100, 0.1 mg/ml BSA and 5 mM 2-mercaptoethanol) and heating the mixture at 95° C. for 6 hours. More specifically, thermostability is determined by measuring DNA polymerase activity after the heat treatment and comparing the value with that before the heat treatment.

Fidelity of DNA Polymerase

In the present invention, "fidelity of DNA polymerase" refers to the accuracy in nucleotide incorporation during DNA replication. Ribosomal protein S12 (rpsL) gene derived from E. coli and relating to streptomycin resistance is used as an indicator to evaluate fidelity of DNA polymerase in the present invention. Streptomycin is an antibiotic which inhibits protein synthesis in prokaryote. Streptomycin binds to 30S ribosomal RNA (rRNA) in prokaryote to thereby inhibit the reaction of producing a protein synthesis initiation complex and cause the misreading of genetic code. Streptomycin-resistant strains have a mutation at ribosome protein S12 locus. It is known that this mutation produces pleiotropic effects for enhancing translation fidelity of ribosome, for example, inhibiting suppressor tRNA from reading the end codon. Thus, when PCR amplification is carried out using rpsL gene as a template, a mutation is introduced with a certain probability. When the mutation occurs at amino acid level, the rpsL protein structure will change so that streptomycin may fail to bind to 30S ribosomal RNA (rRNA). Therefore, when the strain is transformed by an amplified plasmid DNA, appearance frequency of streptomycin-resistant strains increases as more mutation is introduced.

Plasmid pMol 21 (described in *Journal of Molecular Biology* (1999) 289, 835-850) is a plasmid containing rpsL gene and ampicillin resistant gene. The fidelity of DNA replication can be determined by a method comprising the following steps:
(1) designing a primer set (one of the primers is biotinylated and the restriction site of MluI is introduced to the primers) for PCR amplification on the ampicillin resistant gene of the plasmid pMol 21;
(2) amplifying the full-length plasmid by PCR using a thermostable DNA polymerase;
(3) purifying the amplified plasmid using streptavidin beads;
(4) cutting out the amplified plasmid from the streptavidin beads using restriction enzyme MluI;
(5) ligating the ends to form a circular plasmid using DNA ligase to transform *E. coli;*
(6) innoculating the transformant *E. coli* into two kinds of plates (one containing ampicillin and the other containing ampicillin and streptomycin); and
(7) calculating the ratio of numbers of colonies appearing on the plates.

The modified thermostable DNA polymerase of the present invention is an enzyme wherein in the $DX_1EX_2X_3X_4H$ sequence (D: aspartic acid, E: glutamic acid, H: histidine, each of $X_1$, $X_2$, $X_3$ and $X_4$: any amino acid) consisting of $DX_1E$ sequence within the EXO I region and four amino acid length peptide adjacent to said glutamic acid(E) of thermostable DNA polymerase having 3'-5' exonuclease activity, histidine(H) has been replaced by another amino acid. The definition of the EXO I region slightly varies in different reports. However, the $DX_1E$ sequence is commonly included in the EXO I region and the C-terminal of the EXO I region is any one of $X_2$, $X_3$ and $X_4$ in a various reports.

There is no restriction on the origin of thermostable DNA polymerase having the $DX_1EX_2X_3X_4H$ sequence consisting of a part of the C-terminal region of the EXO I region and an amino acid sequence adjacent thereto. Specific examples of thermostable DNA polymerase are KOD DNA polymerase derived from *Pyrococcus kodakaraensis* KOD1, thermostable DNA polymerase derived from *Pyrococcus furiosus*, and thermostable DNA polymerase derived from *Thermococcus litoralis*. According to some recent classification schemes, *Pyrococcus kodakaraensis* is classified as a member of *Thermococcus*.

An exemplary sequence of the $DX_1EX_2X_3X_4H$ sequence is "DIETLYH" (SEQ ID NO:35). This sequence is perfectly preserved in thermostable DNA polymerases derived from *Pyrococcus kodakaraensis* KOD1 and *Pyrococcus furiosus*. Similarly, since the sequence in DNA polymerase derived from *Thermococcus litoralis* is "DIETFYH" (SEQ ID NO: 36), the sequence "DIETLYH" (SEQ ID NO:35) is completely preserved except that L is replaced by F (FIG. 1).

Further, it is easily anticipatable that variants wherein aspartic acid(D) and glutamic acid(E) in the $DX_1EX_2X_3X_4H$ sequence have been replaced by other amino acids are capable of producing similar effects as achieved by the present invention and such variants are included in the present invention.

The "other amino acids" are not particularly limited and include, for example, aspartic acid, glutamic acid and like acidic amino acids; tyrosine, alanine, glycine, valine, leucine, isoleucine, serine, proline, asparagine, glutamine, threonine, cysteine, methionine, tryptophan, phenylalanine and like neutral amino acids; lysine, arginine and like basic amino acids. Particularly preferred are aspartic acid, glutamic acid, tyrosine, alanine, lysine and arginine.

One embodiment of the present invention is a modified thermostable DNA polymerase having significantly reduced 3'-5' exonuclease activity as compared with the enzyme before modification, the reduction of 3'-5' exonuclease activity being achieved by the following modification: in the $DX_1EX_2X_3X_4H$ sequence (D: aspartic acid, E: glutamic acid, H: histidine, $X_1$, $X_2$, $X_3$ and $X_4$: any amino acid) of DNA polymerase having 3'-5' exonuclease activity, histidine(H) is replaced by an acidic amino acid such as glutamic acid or aspartic acid.

Another embodiment of the present invention is a modified thermostable DNA polymerase having improved amplifying efficiency, the improvement being achieved by the following modification: in the $DX_1EX_2X_3X_4H$ sequence (D: aspartic acid, E: glutamic acid, H: histidine, $X_1$, $X_2$, $X_3$ and $X_4$: any amino acid) of DNA polymerase having 3'-5' exonuclease activity, histidine(H) is replaced by an acidic amino acid such as aspartic acid or glutamic acid or a neutral amino acid such as tyrosine or alanine.

A further embodiment of the present invention is a modified thermostable DNA polymerase having significantly improved 3'-5' exonuclease activity and/or fidelity on a DNA replication (amplification), the improvement being achieved by the following modification: in the $DX_1EX_2X_3X_4H$ sequence (D: aspartic acid, E: glutamic acid, H: histidine, $X_1$, $X_2$, $X_3$ and $X_4$: any amino acid) of DNA polymerase having 3'-5' exonuclease activity, histidine(H) has been replaced by a basic amino acid such as lysine or arginine.

More specifically, according to the present invention, 3'-5' exonuclease activity can be reduced by replacing histidine(H) in the $DX_1EX_2X_3X_4H$ sequence (D: aspartic acid, E: glutamic acid, H: histidine, $X_1$, $X_2$, $X_3$ and $X_4$: any amino acid) of thermostable DNA polymerase having 3'-5' exonuclease activity by an acidic amino acid such as aspartic acid or glutamic acid.

Of the variants of the KOD DNA polymerase, variant HE of KOD DNA polymerase (wherein histidine at the 147-position has been replaced by glutamic acid) and variant HD of KOD DNA polymerase (wherein histidine at the 147-position has been replaced by aspartic acid) actually showed about 25% and about 6.25% of 3'-5' exonuclease activity of naturally occurring KOD DNA polymerase, respectively (FIG. 2).

According to the present invention, PCR amplification efficiency from low copy number of template DNA can especially be improved by replacing histidine(H) in the $DX_1EX_2X_3X_4H$ sequence (D: aspartic acid, E: glutamic acid, H: histidine, $X_1$, $X_2$, $X_3$ and $X_4$: any amino acid) of thermostable DNA polymerase having 3'-5' exonuclease activity by an acidic amino acid such as glutamic acid or aspartic acid or a neutral amino acid such as tyrosine or alanine.

Of the variants of the KOD DNA polymerase, variant HE (wherein histidine(H) at the 147-position has been replaced by glutamic acid(E)), variant HD (wherein histidine(H) at the 147-position has been replaced by aspartic acid(D)), variant HY (wherein histidine(H) at the 147-position has been replaced by tyrosine(Y)) and variant HA (wherein histidine (H) at the 147-position has been replaced by alanine(A)) actually showed improved PCR efficiency (FIGS. 3 and 4). Of these variants, particularly variant HY did not show significant reduction in exonuclease activity (FIG. 2), which suggests that histidine at the 147-position affects PCR efficiency independently of its exonuclease activity level. In the amplification of long DNA fragments, especially improved PCR efficiency was observed in variants HE and HD wherein histidine had been replaced by an acidic amino acid (FIG. 4).

Further, according to the present invention, 3'-5' exonuclease activity and/or PCR fidelity of thermostable DNA polymerase can be improved by replacing histidine(H) in the $DX_1EX_2X_3X_4H$ sequence of thermostable polymerase having 3'-5' exonuclease activity by lysine, arginine and like basic amino acids.

Of the variants of KOD DNA polymerase, variant HK (wherein histidine(H) at the 147-position has been replaced by lysine(K)) and variant HR (wherein histidine(H) at the 147-position has been replaced by arginine(R)) according to the present invention actually showed remarkably increased 3'-5' exonuclease activity (FIG. 2). Both variants showed improved PCR fidelity as compared with the naturally occurring DNA polymerase (FIG. 5).

It is easily anticipatable that the improved function (enhanced amplification efficiency, improved fidelity on PCR, etc.) will similarly be produced by replacing histidine at the 147-position by an amino acid other than the above mentioned amino acids.

The DNA extension rate of the modified DNA polymerase of the invention is preferably at least 20 bases/second, more preferably at least 30 bases/second. More specifically, the DNA extension rate is about 20 to about 150 bases/second, preferably about 30 to about 150 bases/second.

The residual polymerase activity of the modified DNA polymerase of the invention after heat treatment (thermostability) is preferably 10% or more, preferably 40% or more, more preferably 60% or more. More specifically, the residual polymerase activity is about 10% to about 100%, preferably about 40% to about 100%, more preferably about 60% to about 100%.

A further embodiment of the present invention is a modified thermostable DNA polymerase wherein in the $DX_1EX_2X_3X_4H$ sequence (D: aspartic acid, E: glutamic acid, H: histidine, $X_1, X_2, X_3$ and $X_4$: any amino acid) consisting of $DX_1E$ sequence within the EXO I region and a four amino acid length peptide adjacent to said glutamic acid(E) of thermostable DNA polymerase having 3'-5' exonuclease activity, histidine(H) has been replaced by another amino acid, the modified thermostable DNA polymerase having the following physicochemical properties:

(1) DNA extension rate: at least 20 bases/second; and
(2) thermostability: it is capable of maintaining 10% or more residual activity at pH 8.8 (determined at 25° C.) after heat treatment at 95° C. for 6 hours (that is, it is capable of retaining 10% or more DNA polymerase activity of untreated DNA polymerase at pH 8.8 (determined at 25° C.) after treatment at 95° C. for 6 hours).

Another embodiment of the present invention is a modified thermostable DNA polymerase wherein in the $DX_1EX_2X_3X_4H$ sequence (D: aspartic acid, E: glutamic acid, H: histidine, $X_1, X_2, X_3$ and $X_4$: any amino acid) consisting of $DX_1E$ sequence within the EXO I region and four amino acid length peptide adjacent to said glutamic acid(E) of thermostable DNA polymerase having 3'-5' exonuclease activity, histidine(H) has been replaced by another amino acid, the modified thermostable DNA polymerase having the following physicochemical properties:

(1) DNA extension rate: at least 30 bases/second; and
(2) thermostability: it is capable of maintaining 40% or more residual activity at pH 8.8 (determined at 25° C.) after heat treatment at 95° C. for 6 hours (that is, it is capable of retaining 40% or more DNA polymerase activity of untreated DNA polymerase at pH 8.8 (determined at 25° C.) after treatment at 95° C. for 6 hours).

A further embodiment of the present invention is a modified thermostable DNA polymerase having the following physicochemical properties:

(1) DNA extension rate: at least 30 bases/second;
(2) thermostability: it is capable of maintaining 60% or more residual activity at pH 8.8 (determined at 25° C.) after heat treatment at 95° C. for 6 hours (that is, it is capable of retaining 60% or more DNA polymerase activity of untreated DNA polymerase at pH 8.8 (determined at 25° C.) after treatment at 95° C. for 6 hours);
(3) optimum temperature: about 65 to 75° C.;
(4) molecular weight: about 89.97 kDa (calculated); at any position other than the histidine site defined below in (5), one or more sugar chains may be deleted or added or one or more amino acids may be deleted, substituted, inserted or added;
(5) amino acid sequence: in the DIETLYH sequence (SEQ ID NO:35) (D: aspartic acid, I: isoleucine, E: glutamic acid, T: threonine, L: leucine, Y: tyrosine, H: histidine) located at the 141- to 147-positions in the amino acid sequence of SEQ ID NO: 2, histidine(H) has been replaced by another amino acid.

A further different embodiment of the present invention is a modified thermostable DNA polymerase having the following physicochemical properties:

(1) DNA extension rate: at least 30 bases/second;
(2) thermostability: it is capable of maintaining 60% or more residual activity at pH 8.8 (determined at 25° C.) after heat treatment at 95° C. for 6 hours (that is, it is capable of retaining 60% or more DNA polymerase activity of untreated DNA polymerase at pH 8.8 (determined at 25° C.) after treatment at 95° C. for 6 hours);
(3) amino acid sequence: the amino acid at the 147-position in the amino acid sequence of SEQ ID NO: 2, namely, histidine(H) has been replaced by another amino acid.

A further embodiment of the invention is a modified thermostable DNA polymerase wherein histidine at the 147-position in the amino acid sequence of SEQ ID NO: 2 has been replaced by an amino acid selected from the group consisting of glutamic acid, aspartic acid, tyrosine, alanine, lysine and arginine.

In the present invention, "the amino acid sequence of SEQ ID NO: 2" includes modified sequence of SEQ ID NO: 2 wherein one or more amino acids other than the histidine residue at the 147-position have been deleted, substituted or added, the modified sequence possessing DNA polymerase activity. Preferable examples of modified sequence of SEQ ID NO: 2 are ones showing 95% or more homology to the amino acid sequence of SEQ ID NO: 2 and possessing DNA polymerase activity, the modification being deletion, substitution or addition of one or more amino acids.

The present invention also provides a gene encoding the thermostable DNA polymerase as shown above.

Process for Preparing Modified DNA Polymerase According to the Invention

To produce these modified enzymes, any of the known methods can be used. For example, there is a technique which introduce a mutation in naturally occurring DNA polymerase so that a modified DNA polymerase having novel activity patterns is produced (*J. Biol. Chem.*, 264(11), 6447-6458 (1989)).

The DNA polymerase-encoding gene in which a mutation is introduced is not particularly limited. Examples of genes include a gene derived from *Pyrococcus kodakaraensis* KOD1 and defined in SEQ ID NO: 3 in the Sequence Listing; a gene derived from *Pyrococcus furiosus* (*Nucleic Acid Res.*, 21 (2), 259-265(1993)); and a gene derived from *Thermococcus litoralis* (*Proc. Natl. Acad. Sci. USA*, 89, 5577-5581 (1992)). To mutate the naturally occurring DNA polymerase gene, any of the known methods can be used. For example, use can be made of a method comprising bringing a drug as a mutagen into contact with the naturally occurring DNA polymerase gene; UV radiation method; or protein engineering techniques such as PCR or site specific mutagenesis.

The QuickChange site-directed mutagenesis kit (Stratagene) used in the present invention makes use of the following steps:

(1) denaturing a plasmid having a target gene inserted therein and annealing mutagenesis primers to the target gene in said plasmid, followed by extending DNA using Pfu DNA polymerase,
(2) repeating the cycle described in (1) 15 times,
(3) selectively cleaving only the template plasmid by using, for example, restriction enzyme DpnI, which recognize the methylated base and
(4) transforming *E. coli* with a newly synthesized plasmid to provide a transformant containing the plasmid mutated as desired.

The modified DNA polymerase gene obtained as described above may be subcloned into an expression vector, if necessary. For example, *E. coli* is transformed with the expression vector and plated on a agar medium containing a drug such as ampicillin to form a colony. The colony is inoculated onto a nutrient medium such as LB medium or 2×YT medium and cultured at 37° C. for 12 to 20 hours. The cultured bacteria were homogenized to extract a crude enzyme solution. Preferable vectors are pLED-MI, pBluescript, or their derivatives.

To homogenize the cultured bacteria, any of the known methods may be used and include, for example, ultrasonication, French Press (High Pressure Homogenizer) glass bead disruption and like physical disruption, or lysis using a lytic enzyme such as lysozyme. The crude enzyme solution is thermally treated, e.g., at 80° C. for 30 minutes to inactivate polymerases derived from the host. After adjusted the DNA polymerase activities of the mutants, 3'-5' exonuclease activities were measured and compared with that of naturally occurring DNA polymerase in order to estimate changing in their 3'-5' exonuclease activities.

To produce a purified DNA polymerase from the strain selected in this manner, any of the known means may be used and include, for example, the following method: The microorganism cultured in media is recovered and treated enzymatically or by physical means so that a crude enzyme solution is extracted. The crude enzyme extract is subjected to heat treatment, e.g., at 80° C. for 30 minutes and the DNA polymerase fraction is recovered by precipitation with sulfate ammonium. This crude enzyme fraction can be desalted by, e.g., gel filtration on Sephadex G-25 (Amersham Pharmacia Biotech).

After this procedure, the desalted enzyme is separated and purified by column chromatography such as Q-Sepharose or heparin-Sepharose to give a purified enzyme preparation. In this process, the enzyme preparation can be purified to such a degree that it shows an almost single band in SDS-PAGE.

By carrying out PCR amplification using the obtained enzyme, PCR efficiency can be evaluated from the occurrence or degree of amplification, and fidelity of DNA replication can also be evaluated.

The modified DNA polymerases of the present invention have excellent DNA amplification efficiency and high amplification fidelity and are suitable for use in PCR.

Nucleic Acid Amplification or Extension Method According to the Invention

The nucleic acid amplification or extension method of the present invention includes a method for synthesizing a DNA primer extension product by reacting DNA as template, one or more kinds of primers and dNTP (i.e., four types of deoxyribonucleoside triphosphates) using the modified thermostable DNA polymerase of the present invention to extend the primers.

There is no specific limitation on the primers in the present invention; however, they should be complementary or substantially complementary to the template DNA.

The method of the invention includes methods for extending nucleic acid using one primer. Such method includes primer extension methods and sequencing methods (including isothermal sequencing and cycle sequencing).

The method of the invention includes methods of amplifying nucleic acid by the PCR method using two or more kinds of primers. Preferably, the primers are 2 kinds of oligonucleotides and each of the primers is complementary to a DNA extension product of the other primer. It is preferable that heating and cooling be carried out repeatedly.

More specifically, the DNA amplification method using PCR is a method which comprises repeating a 3-step cycle comprising denaturation, annealing and extension in the presence of the template DNA, 4 types of deoxyribonucleoside triphosphates, a pair of primers and the modified thermostable DNA polymerase of the present invention to exponentially amplify the template DNA region positioned between the pair of primers (*Nature*, 324 (6093), 13-19(1986)). Stated more specifically, a nucleic acid sample is denatured in the denaturation process; in the following annealing process, each primer is hybridized to a single-stranded template DNA region which is complementary to the primer; in the subsequent extension process, new DNA chains complementary to the single strand template DNA region are extended from each primer by the action of DNA polymerase to provide double-stranded DNA. One double-stranded DNA is amplified to give two double-stranded DNA fragments per cycle. Therefore, if this cycle is repeated n times, the sample DNA region between the pair of primers is theoretically amplified $2^n$ times.

To maintain the activities of the modified DNA polymerase of the invention, it is preferable that divalent ions such as magnesium ions and monovalent ions such as ammonium ions and/or potassium ions are present together with the polymerase of the invention. Further, the PCR reaction solution may include, in addition to such ions, BSA, a nonionic surfactant (e.g. Triton X-100) and a buffer solution. Useful buffer solutions include, for example, good buffers such as Tris and HEPES, and phosphate buffers.

The PCR can be carried out, for example, by repeating a cycle using 3 different temperatures. More specifically, a solution containing a reaction buffer solution (120 mM Tris-HCl (pH 8.0), 10 mM KCl, 6 mM $(NH_4)_2SO_4$, 0.1% TritonX-100, 10 μg/ml BSA), 0.4 pmol/μl each of primers, 0.2 mM dNTPs, 0.2 ng/μl template DNA and 0.05 u/μl modified DNA polymerase of the invention is reacted at 94° C. for 15 seconds, 65° C. for 2 seconds and 74° C. for 30 seconds; and this cycle is repeated about 25 times.

Reagent Kit for Amplifying Nucleic Acid According to the Invention

The reagent kit for amplifying nucleic acid of the present invention comprises 2 kinds of primers, each of the primers being complementary to a DNA extension product of the other primer; dNTP; the modified thermostable DNA polymerase of the invention; divalent ion(s); monovalent ion(s) and a buffer solution. More specifically, the reagent kit for amplifying nucleic acid of the invention comprises 2 kinds of primers, each of the primers being complementary to a DNA extension product of the other primer; dNTP; the above-mentioned modified thermostable DNA polymerase; magnesium ion; at least one ion selected from the group consisting of ammonium ion and potassium ion; BSA; nonionic surfactant(s) and buffer solution(s), as exemplified above.

Another embodiment of the reagent kit for amplifying nucleic acid of the present invention comprises 2 kinds of primers, each of the primers being complementary to a DNA extension product of the other primer; dNTP; the modified thermostable DNA polymerase of the invention; divalent ion(s); monovalent ion(s); buffer solution(s); and optionally an antibody capable of suppressing polymerase activity and/or 3'-5' exonuclease activity of the thermostable DNA polymerase of the invention. Examples of antibodies include monoclonal antibodies, polyclonal antibodies and the like. The reagent kit for amplifying nucleic acid of the present invention is especially effective for enhancing PCR sensitivity and reducing nonspecific amplification.

The reagent kit for amplifying nucleic acid of the present invention further includes core kits which do not contain any primer contained in the above reagent kits. invention The reagent kit for producing a mutated DNA of the present invention comprises mutagenesis primers, each of the primers being complementary to a DNA extension product of the other primer; dNTP; and the modified thermostable DNA polymerase of the present invention. The reagent kit may further include divalent ion(s), monovalent ion(s) and buffer solution, as exemplified above.

According to the present invention, each mutagenesis primer consists of about 20 to about 150 bases and has a mutation (e.g., insertion, deletion or substitution), namely, a mutated site different from the template DNA sequence, near the midpoint of the sequence.

The reagent kit for producing a mutated DNA of the present invention further includes core kits which do not contain any primer contained in the above reagent kits.

Usable as buffer solutions in the nucleic acid amplification reagent kit and the reagent kit for producing a mutated DNA of the present invention are, for example, good buffers such as Tris and HEPES, and phosphate buffers. More specifically, 10 to 200 mM of various buffers (at pH 7.5 to 9.0; determined at 25° C.) may be used.

The concentration of divalent ions such as magnesium ions and manganese ions is preferably 0.5 to 2 mM in the reaction stage. The concentration of monovalent ions such as ammonium ions and potassium ions is preferably about 10 to about 100 mM in the reaction stage.

The concentration of the modified DNA polymerase of the invention is preferably about 0.01 to about 0.1 unit/μl in the reaction stage. The concentration of each of the primers is about 0.2 to about 2 pmol/μl.

Further, the modified thermostable DNA polymerase of the invention can be used as a 3'-5' exonuclease mainly by inactivation or decreasing of its polymerase activity using chemical or genetic engineering techniques.

DNA Polymerase Composition of the Invention

Another embodiment of the invention is a DNA polymerase composition comprising one or more types of modified thermostable DNA polymerases of the present invention as described above. For example, by mixing one or more types of modified thermostable DNA polymerases of the present invention with a DNA polymerase having lower 3'-5' exonuclease activity, there can be provided a composition useful for amplification of long chain (e.g., base length: 4 to 20 kb) nucleic acid (e.g., long PCR). Actually, as a method for amplifying long chain nucleic acid, there is a report on a PCR method using mixed thermostable DNA polymerases (i.e. Taq DNA polymerase (3'-5' exonuclease(−)) and Pfu or Ti DNA polymerase (3'-5' exonuclease(+)) (Barns, W. M. (1994) Proc. Natl. Acad. Sci. USA, 91, 2216-2220). In the present invention, a combination may be, for example, a combination of modified DNA polymerase of the invention with Taq polymerase or with Tth polymerase; and a combination of DNA polymerase of the invention having lower 3'-5' exonuclease activity with DNA polymerase of the invention having higher DNA polymerase.

Other components that may be incorporated into the composition of the invention include, for example, a buffer, divalent ion(s), monovalent ion(s), an antibody to the DNA polymerase, etc.

The present invention is described below in more detail with reference to the Examples.

REFERENCE EXAMPLE 1

Cloning of DNA Polymerase Gene Derived From Hyperthermophilic Archaeon Strain KOD1

Hyperthermophilic archaeon. Pyrococcus kodakaraensis KOD1 strain isolated in Kodakara Island, Kagoshima Prefecture, Japan, was cultured at 95° C. and then recovered. Genomic DNA from Pyrococcus kodakaraensis KOD1 strain was prepared by the conventional manner. Two kinds of primers, i.e., 5'-GGATTAGTATAGTGCCAATGGSSGGCGA-3' and 5'-GAGGGCAGAAGTTTATTCCGAGCTT-3' (SEQ ID NO: 26 and SEQ ID NO: 27; S represents a mixture of C and G) were synthesized based on the conserved region amino acid sequence of DNA polymerase (Pfu DNA polymerase) derived from Pyrococcus furiosus. PCR was conducted using the two kinds of primers and the genomic DNA as a template.

The DNA fragment thus amplified by PCR was sequenced. From the nucleotide sequence thus determined, its amino acid sequence was deduced. Then, the genomic DNA from the KOD1 strain was treated with a restriction enzyme, and the digest was subjected to Southern hybridization with the above amplified DNA fragment as a probe to determine the size of a fragment coding for the DNA polymerase (about 4 to about 7 Kbp). Further, the DNA fragment of this size was recovered from agarose gel and inserted into plasmid pBluescript (Stratagene). The mixture thus obtained was transformed into Escherichia coli JM109 to prepare a library. Colony hybridization with the same probe as in the Southern hybridization was conducted so that a clone strain (E. coli JM109/pBSKOD1) considered to contain the DNA polymerase gene derived from the KOD1 strain was obtained from the library.

Plasmid pBSKOD1 was recovered from the obtained clone strain and sequenced in the usual manner. Its amino acid sequence was deduced from the nucleotide sequence thus determined. The DNA polymerase gene derived from the KOD1 strain consisted of 5010 bases and encoded 1670 amino acids (SEQ ID NO: 1).

2 intervening sequences (1374 to 2453 bp and 2709 to 4316 bp) were removed by PCR fusion method to prepare a complete gene fragment which is free of the intervening sequences, has an EcoRV site at the N-terminal and a BamHI site at the C-terminal, and encodes the DNA polymerase derived from the KOD1 strain (SEQ ID NO: 3). Further, this gene was subcloned in expression vector pET-8c capable of inducing expression of the gene under T7 promoter. A recombinant expression vector (pET-pol) was thus obtained. *E. coli* BL21 (DE3)/pET-pol has been deposited as FERM BP-5513 with the National Institute of Bioscience and Human-Technology, Agency of Industrial Science and Technology, Japan.

EXAMPLE 1

Subcloning of the KOD Polymerase Gene

To modify thermostable DNA polymerase, the KOD DNA polymerase gene was cut out of plasmid pET-pol and subcloned in plasmid pBluescript in the following manner. The KOD DNA polymerase gene, about 2.3 kb long, was cut out by digesting plasmid pET-pol with restriction enzymes XbaI and BamHI (manufactured by Toyobo Co., Ltd.). A ligation kit (Ligation high, manufactured by Toyobo Co., Ltd.) was then used for ligation of this DNA fragment into plasmid pBluescript SK(–) previously digested with XbaI and BamHI. Then, the resulting plasmid was transformed into competent cells (competent high JM109, manufactured by Toyobo Co., Ltd.). The transformant was cultured at 35° C. for 16 hours in an LB agar medium containing 100 μg/ml ampicillin (1% Bacto-trypton, 0.5% yeast extract, 0.5% sodium chloride, 1.5% agar; manufactured by Gibco), and a plasmid was prepared from the resulting colonies. From its partial nucleotide sequence, this plasmid was confirmed to carry the KOD DNA polymerase gene and designated plasmid pKOD1.

EXAMPLE 2

Preparation of Modified Gene (HE) and Purification of Modified Thermostable DNA Polymerase (Variant HE)

Plasmid pKOD1 obtained in Example 1 was used to prepare a plasmid (pKOD HE) carrying a gene encoding a modified thermostable DNA polymerase of KOD DNA polymerase in which histidine(H) at the 147-position had been replaced by glutamic acid(E). To prepare the plasmid, a QuickChange site-directed mutagenesis kit (Stratagene) was used in accordance with the instruction manual. The mutagenesis primers used were primers as shown in SEQ ID NO: 4 and SEQ ID NO: 5. The mutant was confirmed by determining its nucleotide sequence. *E. coli* JM109 was transformed with the resulting plasmid to give *E. coli* JM109 (pKOD HE).

The obtained *E. coli* JM109(pKOD HE) was cultured in the following manner. 6 L of sterilized TB medium containing 100 μg/ml ampicillin (described in *Molecular cloning*, 2nd edition, p. A.2) was introduced into a 10-L jar fermenter. Inoculated into this medium was *E. coli* JM109 (pKOD HE) which had been cultured at 37° C. for 16 hours in 50 ml LB medium (1% Bacto-trypton, 0.5% yeast extract, 0.5% sodium chloride manufactured by Gibco) containing 100 pg/ml ampicillin (using a 500-ml Sakaguchi flask). The microorganism was grown at 35° C. for 12 hours under aeration. The microorganism was recovered from the culture broth by centrifugation, then suspended in 400 ml of a disruption buffer (10 mM Tris-HCl (pH 8.0), 80 mM KCl, 5 mM 2-mercaptoethanol, 1 mM EDTA) and homogenized by French Press (High Pressure Laboratory Homogenizer (Rannie)) to give a cell lysate. The cell lysate was heated at 85° C. for 30 minutes and centrifuged to remove insoluble debris. The supernatant was treated with polyethylene imine for removal of nucleic acids, then precipitated by adding sulfate ammonium and subjected to chromatography on heparin-Sepharose. Finally, the solution was dialized against a storage buffer (50 mM Tris-HCl (pH 8.0), 50 mM potassium chloride, 1 mM dithiothreitol, 0.1% Tween 20, 0.1% Nonidet P40, 50% glycerin) so that the modified thermostable DNA polymerase (variant HE) was obtained. In the purification described above, the measurement of DNA polymerase activity was conducted in the manner as shown below. When the enzyme activity was high, the sample was measured after dilution.

(Reagent)
A: 40 mM Tris-HCl (pH 7.5)
   16 mM magnesium chloride
   15 mM dithiothreitol
   100 μg/ml BSA
B: 2 μg/pl activated calf thymus DNA
C: 1.5 mM dNTP (250 cpm/pmol [$^3$H] dTTP)
D: 20% trichloroacetic acid
   (2 mM sodium pyrophosphate) p1 E: 1 mg/ml salmon sperm DNA (Method)
25 μl of Solution A, 5 μl each of Solutions B and C, and 10 μl sterilized water were added to a microtube and mixed by stirring. Then, 5 μl of the purified enzyme solution (optionally diluted) was added to the mixture and reacted at 75° C. for 10 minutes. The reaction mixture was cooled and 50 μl of Solution E and 100 μl of Solution D were added and stirred, followed by further cooling with ice for 10 minutes. This solution was filtered through a glass filter (Wattman GF/C filter), followed by extensive washing with Solution D and ethanol, and radioactivity of the filter is counted in a liquid scintillation counter (manufactured by Packard) to determine the incorporation of the nucleotide into the template DNA. One unit of enzyme activity was defined as the amount of enzyme that catalyzes the incorporation of 10 nmole of nucleotides into acid-insoluble fraction per 30 minutes under the above-mentioned conditions.

EXAMPLE 3

Preparation of Modified Gene (HD) and Purification of Modified Thermostable DNA Polymerase (Variant HD)

A plasmid (pKOD HD) carrying a gene encoding a modified thermostable DNA polymerase of the KOD DNA polymerase in which histidine(H) at the 147-position had been replaced by aspartic acid(D) was prepared in the same manner as in Example 2. The mutagenesis primers used were primers as shown in SEQ ID NO: 6 and SEQ ID NO: 7. Further, the modified thermostable DNA polymerase (variant HD) was obtained using the same purification method as in Example 2.

EXAMPLE 4

Preparation of Modified Gene (HY) and Purification of Modified Thermostable DNA Polymerase (Variant HY)

A plasmid (pKOD HY) carrying a gene encoding a modified thermostable DNA polymerase of the KOD DNA polymerase in which histidine(H) at the 147-position had been replaced by tyrosine(Y) was prepared in the same manner as in Example 2. The mutagenesis primers used were primers as shown in SEQ ID NO: 8 and SEQ ID NO: 9. Further, the modified thermostable DNA polymerase (variant HY) was obtained using the same purification method as in Example 2.

EXAMPLE 5

Preparation of Modified Gene (HA) and Purification of Modified Thermostable DNA Polymerase (Variant HA)

A plasmid (pKOD HA) carrying a gene encoding a modified thermostable DNA polymerase of the KOD DNA polymerase in which histidine(H) at the 147-position had been replaced by alanine(A) was prepared in the same manner as in Example 2. The mutagenesis primers used were primers as shown in SEQ ID NO: 10 and SEQ ID NO: 11. Further, the modified thermostable DNA polymerase (variant HA) was obtained using the same purification method as in Example 2.

EXAMPLE 6

Preparation of Modified Gene (HK) and Purification of Modified Thermostable DNA Polymerase (Variant HK)

A plasmid (pKOD HK) carrying a gene encoding a modified thermostable DNA polymerase of the KOD DNA polymerase in which histidine(H) at the 147-position had been replaced by lysine(K) was prepared in the same manner as in Example 2. The mutagenesis primers used were primers as shown in SEQ ID NO: 12 and SEQ ID NO: 13. Further, the modified thermostable DNA polymerase (variant HK) was obtained using the same purification method as in Example 2.

Example 7

Preparation of Modified Gene (HR) and Purification of Modified Thermostable DNA Polymerase (Variant HR)

A plasmid (pKOD HR) carrying a gene encoding a modified thermostable DNA polymerase of the KOD DNA polymerase in which histidine(H) at the 147-position had been replaced by arginine(R) was prepared in the same manner as in Example 2. The mutagenesis primers used were primers as shown in SEQ ID NO: 14 and SEQ ID NO: 15. Further, the modified thermostable DNA polymerase (variant HR) was obtained using the same purification method as in Example 2.

EXAMPLE 8

Preparation of Modified Gene (HS) and Purification of Modified Thermostable DNA Polymerase (Variant HS)

A plasmid (pKOD HS) carrying a gene encoding a modified thermostable DNA polymerase of the KOD DNA polymerase in which histidine(H) at the 147-position had been replaced by serine(S) was prepared in the same manner as in Example 2. The mutagenesis primers used were primers as shown in SEQ ID NO: 16 and SEQ ID NO: 17. Further, the modified thermostable DNA polymerase (variant HS) was obtained using the same purification method as in Example 2.

EXAMPLE 9

Preparation of Modified Gene (HO) and Purification of Modified Thermostable DNA Polymerase (Variant HO)

A plasmid (pKOD HQ) carrying a gene encoding a modified thermostable DNA polymerase of the KOD DNA polymerase in which histidine(H) at the 147-position had been replaced by glutamine(Q) was prepared in the same manner as in Example 2. The mutagenesis primers used were primers as shown in SEQ ID NO: 18 and SEQ ID NO: 19. Further, the modified thermostable DNA polymerase (variant HQ) was obtained using the same purification method as in Example 2.

EXAMPLE 10

Comparison of 3'-5' Exonuclease Activity Between Modified Thermostable DNA Polymerases The exonuclease activities of the modified thermostable DNA polymerases obtained in Examples 2 to 9 and variants IK and IQ were determined in the following manner. The variants IK and IQ were prepared from KOD DNA polymerase described in Japanese Unexamined Patent Publication No. 1998-42871 by replacing isoleucine at the 142-position with lysine and glutamine respectively in accordance with the method described in Japanese Unexamined Patent Publication No. 1998-42871 (namely, variants IK and IQ were the KOD DNA polymerase-variants in which isoleucine (I) at the 142-position have been replaced by lysine(K) and glutamine(Q),respectively.) As a control, the naturally occurring KOD DNA polymerase (Toyobo Co., Ltd.) was used.

50 μl of a reaction solution (120 mM Tris-HCl (pH 8.8 at 25° C.), 10 mM KCl, 6 mM ammonium sulfate, 1 mM MgCl$_2$, 0.1% Triton X-100, 0.001% BSA, 5 μg tritium-labeled *E. coli* DNA) was pipetted into each of 1.5-ml microtubes. 0.06 U or 0.025 U of each DNA polymerase was added to the reaction mixture. The mixture was reacted at 75° C. for 10 minutes and then cooled with ice to terminate the reaction. After 50 μl of 0.1% BSA was added as a carrier, 100 μl of a solution containing 10% trichloroacetic acid and 2% sodium pyrophosphate was further added and mixed. The mixture was left on ice for 15 minutes and then centrifuged at 12,000 r.p.m. for 10 minutes to separate precipitates. The radioactivity of 100 μl of the supernatant was measured in a liquid scintillation counter (Packard) whereby the amount of the nucleotide delivered into the acid-soluble fraction was determined. Based on the radioactivities from 0.06 U and 0.025 U (polymerase unit) of mutated enzymes, relative 3'-5' exonuclease activities were estimated. FIG. 2 shows relative exonuclease activities of the DNA polymerases.

The results proved that thermostable DNA polymerases with 3'-5' exonuclease activity at different levels can be produced by the present invention. As compared with the naturally occurring KOD DNA polymerase (100%), the modified thermostable DNA polymerases had 3'-5' exonuclease activity at the following levels: variant HD had about 6.25%; variant HE about 25%; variant HY about 90%; variant HA about 30%; variant HS about 50%; variant HQ about 50%;

variant HK about 400%; variant HR about 300%; variant IK about 6.25%; and variant IQ about 25%.

EXAMPLE 11

Confirmation of Thermostability

The thermostability of the modified thermostable DNA polymerases obtained in Examples 2, 3 and 6 was determined in the following manner. 5 units of each purified modified DNA polymerase was mixed with 100 µl of a buffer solution (20 mM Tris-HCl pH 8.8 at 25° C., 10 mM potassium chloride, 10 mM ammonium sulfate, 2 mM magnesium sulfate, 0.1% Triton X-100, 0.1 mg/ml BSA, 5 mM 2-mercaptoethanol) and pre-incubated at 95° C. A sample was recovered from this mixture with time, and its polymerase activity was determined in the method described in Example 2. For comparison, a naturally occurring KOD DNA polymerase (Toyobo Co., Ltd.) and Taq DNA polymerase were also subjected to the same procedure. Table 1 shows that similar to the naturally occurring KOD DNA polymerase, any of the modified thermostable DNA polymerases had 60% or more residual activity after treatment at 95° C. for 6 hours.

TABLE 1

| DNA polymerase | Residual DNA polymerase activity |
| --- | --- |
| Naturally occurring KOD DNA polymerase | 70% |
| Example 2 | 84% |
| Example 3 | 77% |
| Example 6 | 68% |
| Taq DNA polymerase | 10% |

EXAMPLE 12

Measurement of DNA Extension Rate

The modified thermostable DNA polymerases obtained in Examples 2, 3, 6 and 7 were examined for DNA extension rate in the following manner. 1 unit of each purified modified DNA polymerase was reacted with single stranded M13mp18 DNA to which 0.2 µg of the primer (SEQ ID NO: 28) had been annealed. The reaction was carried out in 10 µl of a reaction solution (20 mM Tris-HCl (pH 7.5), 8 mM magnesium chloride, 7.5 mM dithiothreitol, 100 µg/ml BSA, 0.1 mM dNTP, 0.2 µCi [α-$^{32}$P]dCTP) at 75° C. for 20, 40, and 60 seconds respectively. The reaction was terminated by adding an equal volume (equal to the reaction mixture) of a reaction-terminating solution (50 mM sodium hydroxide, 10 mM EDTA, 5% Ficoll, 0.05% Bromophenol Blue). For comparison, Pfu DNA polymerase (Stratagene) and the naturally occurring KOD DNA polymerase (Toyobo Co., Ltd.) were subjected to the same procedure.

The DNA fragments are sized by electrophoresis on an alkaline agarose gel, and the gel was dried and subjected to autoradiography. As a DNA size marker, labeled λ/HindIII was used. The DNA extension rate was determined by measuring the size of the synthesized DNA using a band of this marker as an indicator. Table 2 shows the results. Similar to the naturally occurring KOD DNA polymerase, any of the modified DNA polymerases had an extension rate of about 120 bases/second. By contrast, Pfu DNA polymerase had an extension rate of about 20 bases/second.

TABLE 2

| DNA polymerase | Extension rate (base/sec.) |
| --- | --- |
| Naturally occurring KOD DNA polymerase | 120 |
| Example 2 | 123 |
| Example 3 | 123 |
| Example 6 | 123 |
| Example 7 | 120 |
| Pfu DNA polymerase | 20 |

EXAMPLE 13

PCR (1) by Use of Modified DNA Polymerases

PCR was carried out using naturally occurring KOD DNA polymerase (hereinafter sometimes referred to as "WT") and modified thermostable DNA polymerases (variants HE, HD, HY, HA, HK, HR, IK and IQ). The variants IK and IQ were prepared from KOD DNA polymerase described in Japanese Unexamined Patent Publication No. 1998-42871 by replacing isoleucine(I) at the 142-position with lysine(K) and glutamine(Q) respectively. It is known that variants HE and IQ have a similar level of 3'-5' exonuclease activity and variants HD and IK have a similar level of 3'-5' exonuclease activity.

1 µl (1 U/µl) of each enzyme was added to 49 µl of a reaction solution (1×KOD-Plus-buffer (Toyobo Co., Ltd.), 1 mM MgSO$_4$, 0.2 mM dNTP, 100 ng and 10 ng K562 DNA (Life Technologies, Inc.), and 10 pmol each of primers shown in SEQ ID NO: 20 and SEQ ID NO: 21). Using PCR system GeneAmp2400 (Perkin-Elmer Corp.) as a thermal cycler, the PCR amplification reaction was conducted under the following conditions. The reaction was carried out at 94° C. for 2 minutes, followed by a cycle consisting of reaction at 94° C. for 15 seconds, at 60° C. for 30 seconds and at 68° C. for 3 minutes and 30 seconds. This cycle was repeated 30 times. After completion of the reaction, 10 µl of the reaction solution was subjected to agarose gel electrophoresis and dyed with ethidium bromide. Under UV irradiation, amplification of about 3.6 kb target DNA fragment was confirmed. FIG. 3 shows the result of agarose gel electrophoresis. The result proved that as compared with the naturally occurring KOD DNA polymerase, variants HE, HD, HY and HA especially improve PCR amplification of low copy number of template DNA (10 ng).

EXAMPLE 14

PCR (2) by Use of Modified DNA Polymerase

Using the modified thermostable polymerases, variants HE, HD, HY and HA which had achieved good results in Example 13, amplification of larger size DNA was attempted.

1 µl (1 U/µl) of each enzyme was added to 49 µl of a reaction solution (1×KOD-Plus-buffer (Toyobo Co., Ltd.), 1 mM MgSO$_4$, 0.2 mM dNTP, 100 ng and 50 ng K562 DNA (Life Technologies, Inc.), and 10 pmol each of primers shown in SEQ ID NO: 22 and SEQ ID NO: 23). Using PCR system GeneAmp2400 (Perkin-Elmer Corp.) as a thermal cycler, the PCR amplification reaction was conducted under the following conditions. The reaction was carried out at 94° C. for 2 minutes, followed by a cycle consisting of reaction at 94° C. for 15 seconds, at 60° C. for 30 seconds and at 68° C. for 6 minutes. This cycle was repeated 30 times. After completion of the reaction, 10 μl of the reaction solution was subjected to agarose gel electrophoresis and dyed with ethidium bromide. Under UV irradiation, amplification of about 6.2 kb target DNA fragment was confirmed. Variants HD and HE produced especially good amplification results (FIG. 4). Amplification using naturally occurring KOD DNA polymerase (WT) could not be detected (not shown in FIG. 4).

EXAMPLE 15

Measurement of Modified KOD DNA Polymerase Fidelity

The fidelity of naturally occurring KOD DNA polymerase and modified thermostable DNA polymerases was measured in the following manner. 1 μl (1 U/μl) of each enzyme was added to 49 μl of a reaction solution (1×KOD-Plus-buffer (Toyobo Co., Ltd.), 1 mM $MgSO_4$, 0.2 mM dNTP, 2.5 ng plasmid pMol 21 (*Journal of Molecular Biology* (1999) 289, 835-850), and 10 pmol each of primers shown in SEQ ID NO: 24 and SEQ ID NO: 25). The PCR amplification reaction was conducted under the following conditions using variants HD, HE, HY, HA, HK and HR among the obtained variants, and variants IK and IQ described in Japanese Unexamined Patent Publication No. 1998-42871. Using PCR system Gene-Amp2400 (Perkin-Elmer Corp.) as a thermal cycler, the PCR was carried out under the following conditions. The reaction was carried out at 94° C. for 2 minutes, followed by a cycle consisting of reaction at 94° C. for 15 seconds, at 60° C. for 30 seconds and at 68° C. for 4 minutes. This cycle was repeated 25 times. At the same time, an amplification reaction using rTaq DNA polymerase was carried out under the following reaction conditions. 0.5 μl (5 U/μl) of Taq DNA polymerase was added to 49 μl of a reaction solution (1×rTaq buffer (Toyobo Co., Ltd.), 1.5 mM $MgCl_2$, 0.2 mM dNTP, 2.5 ng plasmid pMol 21 (*Journal of Molecular Biology* (1999) 289, 835-850), and 10 pmol each of primers shown in SEQ ID NOS: 24 and 25). The PCR reaction was carried out at 94° C. for 2 minutes, followed by a cycle consisting of reaction at 94° C. for 15 seconds, at 60° C. for 30 seconds and at 68° C. for 5 minutes. This cycle was repeated 25 times.

After completion of PCR, the reaction mixture was treated with phenol/chloroform and DNA was precipitated with ethanol. The precipitates were dissolved in 100 μl of distilled water. To the solution were added 10 μl of avidin magnetic beads (manufactured by DYNAL). The mixture was subjected to invert blending for 30 minutes. The magnetic beads were concentrated using a magnetic separation stand (Magical Trapper; product of Toyobo Co., Ltd.). After discarding the supernatant, 100 μl of wash A (10 mM Tris-HCl, (pH 8.0), 1 mM EDTA and 1M NaCl) was added to the magnetic beads, followed by stirring for 10 seconds and the magnetic beads were concentrated again using the magnetic separation stand and the supernatant was discarded (washing process). The washing process was repeated once again and then the magnetic beads were washed with wash B(10 mM Tris-HCl (pH 8.0), 1 mM EDTA). Only the magnetic beads were collected using the magnetic separation stand and subsequently, 40 μl of distilled water, 5 μl of a restriction enzyme buffer solution and 50 U of restriction enzyme Mlu I (Toyobo Co., Ltd.) were added to the beads. The treatment was allowed to proceed with invert-mixing at 37° C. for 3 hours. Then, the magnetic beads were concentrated again using the magnetic separation stand and only the supernatant was collected. The collected DNA solution was desalted by the ethanol precipitation method. To a 10 ng quantity of the desalted solution was added a ligation reagent (Ligation high, manufactured by Toyobo Co., Ltd.). A ligation reaction was allowed to proceed at 16° C. for 16 hours. The resulting DNA was transformed into competent cells of *E. coli* MF-101 (*Journal of Molecular Biology* (1999) 289, 835-850) prepared by the method described in *Molecular cloning* 2nd edition 1.74-1.81.

The transformed *E. coli* solution was divided into two. One was cultured on an LB agar medium (0.6%) <plate A> containing 200 μg/ml of ampicillin at 30° C. for 24 hours, whereas the other was cultured on an LB agar medium (0.6%) <plate B> containing 200 μg/ml of ampicillin and 400 μg/ml of streptomycin at 30° C. for 24 hours. The number of colonies appearing on the plates were counted. Mutation frequency (%) was calculated by dividing the number of colonies on plate B by the number on plate A and expressed in percentage terms (multiplied by 100). A lower mutation frequency indicates a higher DNA polymerase fidelity in DNA replication.

FIG. 5 shows the results. rTaq polrmerase free of 3'-5' exonuclease (proof-reading) activity showed a high mutation frequency of 7.91%. By contrast, all the variants obtained according to the present invention and naturally occurring DNA polymerase (WT) showed 1% or less mutation frequency. Among them, variants HK and HR having increased 3'-5' exonuclease activity as compared with naturally occurring DNA polymerase showed mutation frequency of 0.12% and 0.17% respectively, which are remarkable good values as compared with a mutation frequency of 0.47% achieved with naturally occurring DNA polymerase.

As shown above, the present invention achieved production of thermostable DNA polymerases with different levels of DNA amplification efficiency, 3'-5' exonuclease activity and fidelity. The method of the present invention comprising modification of conventional archaebacteria-derived thermostable DNA polymerases produces modified thermostable DNA polymerases that are useful for various purposes such as long template amplification and high fidelity amplification.

A: PCR using 100 ng of human cell line K562-derived DNA

B: PCR using 10 ng of human cell line K562-derived DNA

1: naturally occurring DNA polymerase (WT),
2: variant HD,
3: variant HE,
4: variant HY,
5: variant HA,
6: variant HK,
7: variant HR,
8: variant IK,
9: variant IQ.

Figures 1, 2:
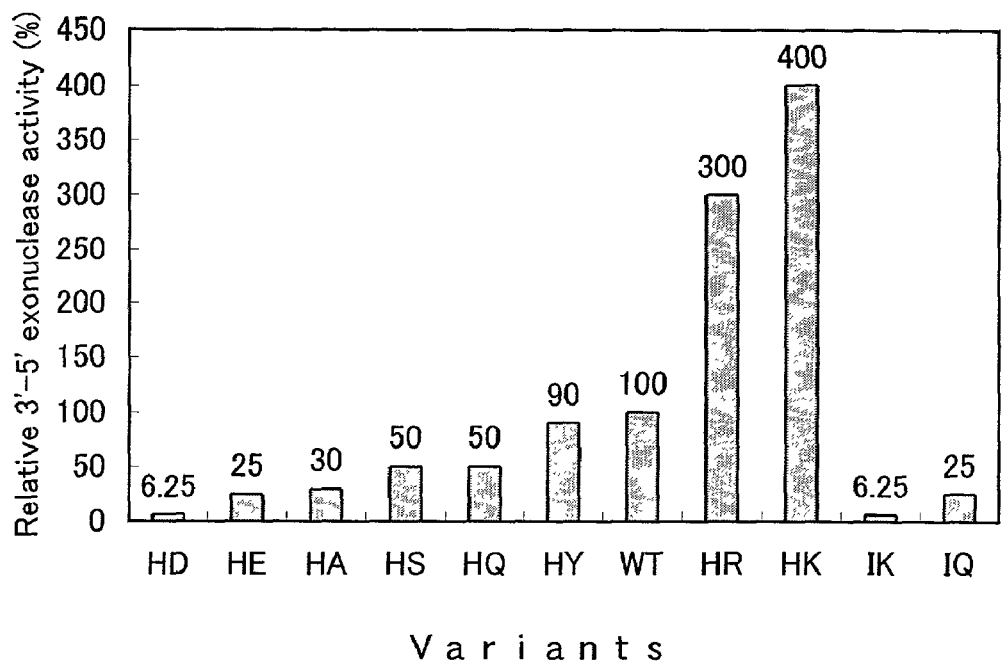
FIG. 1 shows the EXO I region (underlined) and amino acid sequence adjacent to the EXO I region in various DNA polymerases.
FIG. 2 shows relative 3'-5' exonuclease activities in various KOD DNA polymerase variants (calculated relative to the activity of WT as 100).
Figure 3:
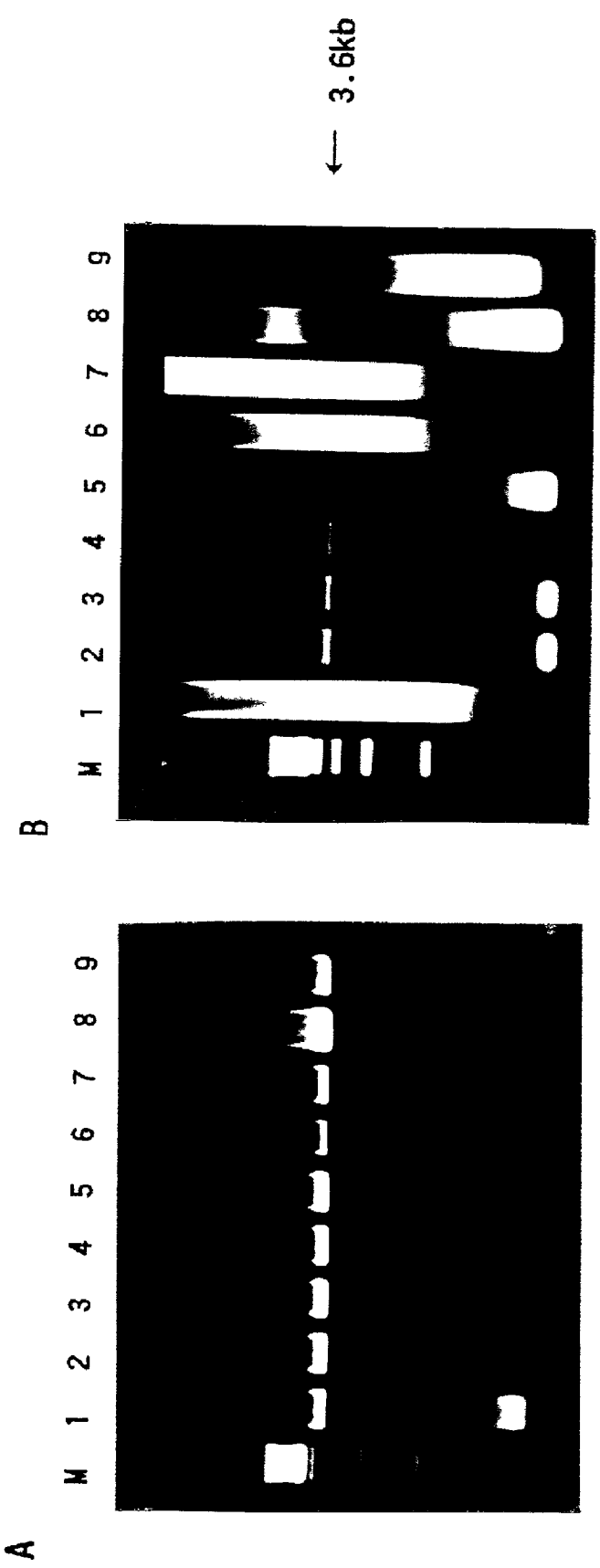
FIG. 3 shows the result of PCR amplification of β-globin gene (3.6 kb) using human genome DNA as a template and various KOD DNA polymerase variants.
Figure 4:
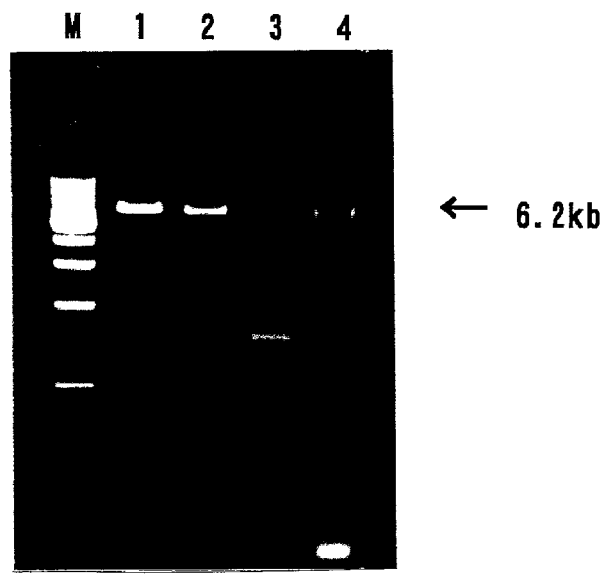

FIG. 4 shows the result of the PCR amplification of Myosin heavy chain gene (6.2 kb) using human genome DNA as a template and various modified KOD DNA polymerases.

PCR using 50 ng of human cell line K562-extracted DNA
1: variant HD,
2: variant HE,
3: variant HY,
4: variant HA.

Figure 5:
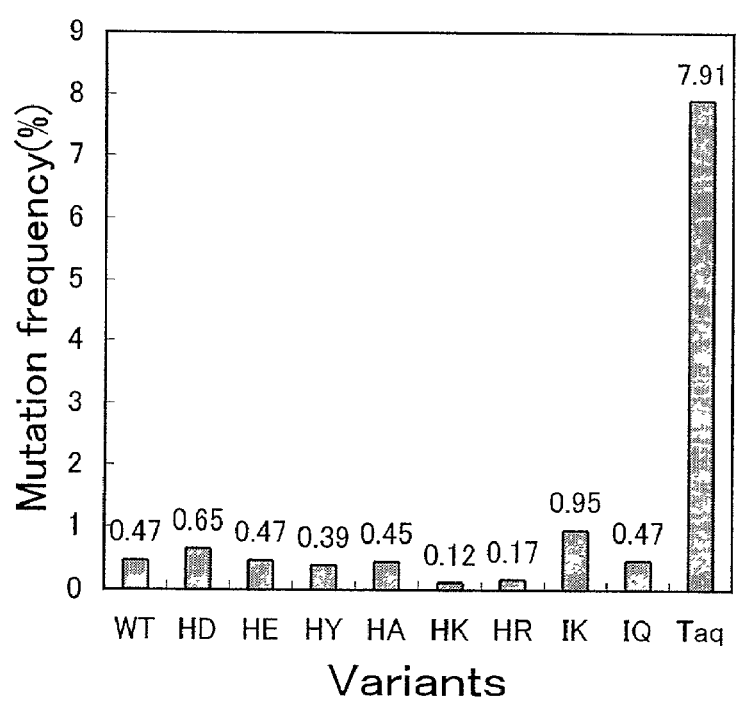

FIG. 5 shows mutation frequency (%) in PCR amplification using various KOD DNA polymerase variants.

The invention claimed is:

1. A thermostable DNA polymerase having a 3'-5' exonuclease activity and the amino acid sequence of a thermostable DNA polymerase of *Pyrococcus furiosus*, *Pyrococcus kodakaraensis* KOD 1 or *Thermococcus litoralis*, with a single modification, wherein the modification is a replacement of histidine (H) in the DIETLYH (SEQ ID NO:35) or DIETFYH (SEQ ID NO:36) sequence (D: aspartic acid, I: isoleucine, E: glutamic acid, T: threonine, L: leucine, F: phenylalanine, Y: tyrosine, H: histidine) within the exonuclease I region by another amino acid.

2. The thermostable DNA polymerase according to claim 1, wherein in the DIETLYH (SEQ ID NO:35) or DIETFYH (SEQ ID NO:36) sequence, histidine (H) has been replaced by an amino acid selected from the group consisting of aspartic acid, glutamic acid, tyrosine, alanine, lysine and arginine.

3. The thermostable DNA polymerase according to claim 1 having the following physicochemical properties:
(1) DNA extension rate: at least 20 bases/second; and
(2) thermostability: it is capable of retaining 1000 or more DNA polymerase activity of untreated DNA polymerase at pH 8.8 (determined at 25° C.) after treatment at 95° C. for 6 hours.

4. A thermostable DNA polymerase having a 3'-5' exonuclease activity and the following physicochemical properties:
(1) DNA extension rate: at least 30 bases/second;
(2) thermostability: the modified thermostable DNA polymerase being capable of retaining 40% or more DNA polymerase activity of untreated DNA polymerase at pH 8.8 (determined at 25° C.) after treatment at 95° C. for 6 hours; and
(3) amino acid sequence: the thermostable DNA polymerase comprising the amino acid sequence of SEQ ID NO:2, except that histidine (H) at the 147-position of SEQ ID NO:2 has been replaced by another amino acid.

5. The thermostable DNA polymerase according to claim 4 having the following thermostability: it is capable of retaining 60% or more DNA polymerase activity of untreated DNA polymerase at pH 8.8 (determined at 25° C.) after treatment at 95° C. for 6 hours.

6. The thermostable DNA polymerase according to claim 5, wherein histidine (H) at the 147-position has been replaced by an amino acid selected from the group consisting of aspartic acid, glutamic acid, tyrosine, alanine, lysine and arginine.

7. The thermostable DNA polymerase according to claim 6, wherein histidine (H) at the 147-position has been replaced by aspartic acid.

8. The thermostable DNA polymerase according to claim 6, wherein histidine (H) at the 147-position has been replaced by glutamic acid.

9. The thermostable DNA polymerase according to claim 6, wherein histidine (H) at the 147-position has been replaced by tyrosine.

10. The thermostable DNA polymerase according to claim 6, wherein histidine (H) at the 147-position has been replaced by alanine.

11. The thermostable DNA polymerase according to claim 6, wherein histidine (H) at the 147-position has been replaced by lysine.

12. The thermostable DNA polymerase according to claim 6, wherein histidine (H) at the 147-position has been replaced by arginine.

13. A reagent kit for amplifying nucleic acid, which comprises 2 kinds of primers, each of the primers being complementary to a DNA extension product of the other primer; dNTP; the thermostable DNA polymerase of claim 1; divalent ion(s); monovalent ion(s); and a buffer solution.

14. A reagent kit for amplifying nucleic acid, which comprises 2 kinds of primers, each of the primers being complementary to a DNA extension product of the other primer; dNTP; the thermostable DNA polymerase of claim 1; magnesium ion; at least one of monovalent ions selected from the group consisting of ammonium ion and potassium ion; BSA (bovine serum albumin); a nonionic surfactant and a buffer solution.

15. A reagent kit for amplifying nucleic acid, which comprises 2 kinds of primers, each of the primers being complementary to a DNA extension product of the other primer; dNTP; the thermostable DNA polymerase of claim 1; magnesium ion; at least one of monovalent ions selected from the group consisting of ammonium ion and potassium ion; BSA (bovine serum albumin); a nonionic surfactant; a buffer solution and an antibody capable of suppressing at least one activity selected from polymerase activity and 3'-5' exonuclease activity of the thermostable DNA polymerase.

16. A DNA polymerase composition which comprises at least one of the thermostable DNA polymerases of claim 1.

17. A reagent kit for producing a mutated DNA which comprises mutagenesis primers, dNTP and the thermostable DNA polymerase of claim 1.

18. A thermostable DNA polymerase according to claim 1, wherein said DNA polymerase is an α-like DNA polymerase.

19. A thermostable DNA polymerase according to claim 1, wherein the histidine (H) has been replaced by an acidic amino acid to obtain the thermostable DNA polymerase with the modification having significantly reduced 3'-5' exonuclease activity as compared with the thermostable DNA polymerase without the modification.

20. A thermostable DNA polymerase according to claim 1, wherein the histidine (H) has been replaced by a neutral amino acid to obtain the thermostable DNA polymerase with the modification having improved amplifying efficiency compared with the thermostable DNA polymerase without the modification.

21. A thermostable DNA polymerase according to claim 1, wherein the histidine (H) has been replaced by a basic amino acid to obtain the thermostable DNA polymerase with the modification having significantly improved 3'-5' exonuclease activity and/or fidelity on DNA replication or amplification compared with the thermostable DNA polymerase without the modification.

22. The thermostable DNA polymerase according to claim 1, wherein the histidine (H) has been replaced by an acidic amino acid to obtain the thermostable DNA polymerase with the modification having improved PCR amplifcation efficiency from low copy number of template DNA compared with the thermostable DNA polymerase without the modification.

23. The thermostable DNA polymerase according to claim 1, wherein the histidine (H) has been replaced by an acidic amino acid to obtain the thermostable DNA polymerase with the modification having improved PCR amplifcation efficiency from a long DNA segment compared with the thermostable DNA polymerase without the modification.

24. The thermostable DNA polymerase according to claim 1, wherein the histidine (H) has been replaced by a neutral amino acid to obtain the thermostable DNA polymerase with the modification having improved PCR amplifcation efficiency from low copy number of template DNA compared with the thermostable DNA polymerase without the modification.

25. A thermostable DNA polymerase having a 3'-5' exonuclease activity and the amino acid sequence of a thermostable DNA polymerase of *Pyrococcus kodakaraensis* KOD 1 with a single modification, wherein the modification is a replacement of histidine (H) in the DIETLYH sequence (SEQ ID NO:35) in SEQ ID NO:2 (D: aspartic acid, I: isoleucine, E: glutamic acid, T: threonine, L: leucine, Y: tyrosine, H: histidine) within the exonuclease I region by another amino acid.

* * * * *

SEQUENCE LISTING

<160> NUMBER OF SEQ ID NOS: 28

<210> SEQ ID NO 1
<211> LENGTH: 5342
<212> TYPE: DNA
<213> ORGANISM: Pyrococcus kodakaraensis
<220> FEATURE:
<221> NAME/KEY: CDS
<222> LOCATION: (156)..(5165)
<223> OTHER INFORMATION: 1374-2453 intron, 2709-4316 intron

<400> SEQUENCE: 1

```
gcttgagggc ctgcggttat gggacgttgc agtttgcgcc tactcaaaga tgccggtttt      60
ataacggaga aaaatgggga gctattacga tctctccttg atgtgggggtt tacaataaag    120 cctggattgt tctacaagat tatgggggat gaaag atg atc ctc gac act gac       173
                                      Met Ile Leu Asp Thr Asp
                                        1               5 tac ata acc gag gat gga aag cct gtc ata aga att ttc aag aag gaa      221
Tyr Ile Thr Glu Asp Gly Lys Pro Val Ile Arg Ile Phe Lys Lys Glu
        10                  15                  20 aac ggc gag ttt aag att gag tac gac cgg act ttt gaa ccc tac ttc      269
Asn Gly Glu Phe Lys Ile Glu Tyr Asp Arg Thr Phe Glu Pro Tyr Phe
25                  30                  35 tac gcc ctc ctg aag gac gat tct gcc att gag gaa gtc aag aag ata      317
Tyr Ala Leu Leu Lys Asp Asp Ser Ala Ile Glu Glu Val Lys Lys Ile
            40                  45                  50 acc gcc gag agg cac ggg acg gtt gta acg gtt aag cgg gtt gaa aag      365
Thr Ala Glu Arg His Gly Thr Val Val Thr Val Lys Arg Val Glu Lys
55                  60                  65                  70 gtt cag aag aag ttc ctc ggg aga cca gtt gag gtc tgg aaa ctc tac      413
Val Gln Lys Lys Phe Leu Gly Arg Pro Val Glu Val Trp Lys Leu Tyr
                75                  80                  85 ttt act cat ccg cag gac gtc cca gcg ata agg gac aag ata cga gag      461
Phe Thr His Pro Gln Asp Val Pro Ala Ile Arg Asp Lys Ile Arg Glu
            90                  95                 100 cat ggg gca gtt att gac atc tac gag tac gac ata ccc ttc gcc aag      509
His Gly Ala Val Ile Asp Ile Tyr Glu Tyr Asp Ile Pro Phe Ala Lys
            105                 110                 115 cgc tac ctc ata gac aag gga tta gtg cca atg gaa ggc gac gag gag      557
Arg Tyr Leu Ile Asp Lys Gly Leu Val Pro Met Glu Gly Asp Glu Glu
        120                 125                 130 ctg aaa atg ctc gcc ttc gac att gaa act ctc tac cat gag ggc gag      605
Leu Lys Met Leu Ala Phe Asp Ile Glu Thr Leu Tyr His Glu Gly Glu
135                 140                 145                 150 gag ttc gcc gag ggg cca atc ctt atg ata agc tac gcc gac gag gaa      653
Glu Phe Ala Glu Gly Pro Ile Leu Met Ile Ser Tyr Ala Asp Glu Glu
                155                 160                 165 ggg gcc agg gtg ata act tgg aag aac gtg gat ctc ccc tac gtt gac      701
Gly Ala Arg Val Ile Thr Trp Lys Asn Val Asp Leu Pro Tyr Val Asp
            170                 175                 180 gtc gtc tcg acg gag agg gag atg ata aag cgc ttc ctc cgt gtt gtg      749
Val Val Ser Thr Glu Arg Glu Met Ile Lys Arg Phe Leu Arg Val Val
            185                 190                 195 aag gag aaa gac ccg gac gtt ctc ata acc tac aac ggc gac aac ttc      797
Lys Glu Lys Asp Pro Asp Val Leu Ile Thr Tyr Asn Gly Asp Asn Phe
        200                 205                 210 gac ttc gcc tat ctg aaa aag cgc tgt gaa aag ctc gga ata aac ttc      845
Asp Phe Ala Tyr Leu Lys Lys Arg Cys Glu Lys Leu Gly Ile Asn Phe
215                 220                 225                 230
```

-continued

```
gcc ctc gga agg gat gga agc gag ccg aag att cag agg atg ggc gac      893
Ala Leu Gly Arg Asp Gly Ser Glu Pro Lys Ile Gln Arg Met Gly Asp
                235                 240                 245 agg ttt gcc gtc gaa gtg aag gga cgg ata cac ttc gat ctc tat cct      941
Arg Phe Ala Val Glu Val Lys Gly Arg Ile His Phe Asp Leu Tyr Pro
        250                 255                 260 gtg ata aga cgg acg ata aac ctg ccc aca tac acg ctt gag gcc gtt      989
Val Ile Arg Arg Thr Ile Asn Leu Pro Thr Tyr Thr Leu Glu Ala Val
    265                 270                 275 tat gaa gcc gtc ttc ggt cag ccg aag gag aag gtt tac gct gag gaa     1037
Tyr Glu Ala Val Phe Gly Gln Pro Lys Glu Lys Val Tyr Ala Glu Glu
280                 285                 290 ata acc aca gcc tgg gaa acc ggc gag aac ctt gag aga gtc gcc cgc     1085
Ile Thr Thr Ala Trp Glu Thr Gly Glu Asn Leu Glu Arg Val Ala Arg
295                 300                 305                 310 tac tcg atg gaa gat gcg aag gtc aca tac gag ctt ggg aag gag ttc     1133
Tyr Ser Met Glu Asp Ala Lys Val Thr Tyr Glu Leu Gly Lys Glu Phe
            315                 320                 325 ctt ccg atg gag gcc cag ctt tct cgc tta atc ggc cag tcc ctc tgg     1181
Leu Pro Met Glu Ala Gln Leu Ser Arg Leu Ile Gly Gln Ser Leu Trp
        330                 335                 340 gac gtc tcc cgc tcc agc act ggc aac ctc gtt gag tgg ttc ctc ctc     1229
Asp Val Ser Arg Ser Ser Thr Gly Asn Leu Val Glu Trp Phe Leu Leu
    345                 350                 355 agg aag gcc tat gag agg aat gag ctg gcc ccg aac aag ccc gat gaa     1277
Arg Lys Ala Tyr Glu Arg Asn Glu Leu Ala Pro Asn Lys Pro Asp Glu
360                 365                 370 aag gag ctg gcc aga aga cgg cag agc tat gaa gga ggc tat gta aaa     1325
Lys Glu Leu Ala Arg Arg Arg Gln Ser Tyr Glu Gly Gly Tyr Val Lys
375                 380                 385                 390 gag ccc gag aga ggg ttg tgg gag aac ata gtg tac cta gat ttt aga     1373
Glu Pro Glu Arg Gly Leu Trp Glu Asn Ile Val Tyr Leu Asp Phe Arg
            395                 400                 405 tgc cat cca gcc gat acg aag gtt gtc gtc aag ggg aag ggg att ata     1421
Cys His Pro Ala Asp Thr Lys Val Val Val Lys Gly Lys Gly Ile Ile
        410                 415                 420 aac atc agc gag gtt cag gaa ggt gac tat gtc ctt ggg att gac ggc     1469
Asn Ile Ser Glu Val Gln Glu Gly Asp Tyr Val Leu Gly Ile Asp Gly
    425                 430                 435 tgg cag aga gtt aga aaa gta tgg gaa tac gac tac aaa ggg gag ctt     1517
Trp Gln Arg Val Arg Lys Val Trp Glu Tyr Asp Tyr Lys Gly Glu Leu
440                 445                 450 gta aac ata aac ggg tta aag tgt acg ccc aat cat aag ctt ccc gtt     1565
Val Asn Ile Asn Gly Leu Lys Cys Thr Pro Asn His Lys Leu Pro Val
455                 460                 465                 470 gtt aca aag aac gaa cga caa acg aga ata aga gac agt ctt gct aag     1613
Val Thr Lys Asn Glu Arg Gln Thr Arg Ile Arg Asp Ser Leu Ala Lys
            475                 480                 485 tct ttc ctt act aaa aaa gtt aag ggc aag ata ata acc act ccc ctt     1661
Ser Phe Leu Thr Lys Lys Val Lys Gly Lys Ile Ile Thr Thr Pro Leu
        490                 495                 500 ttc tat gaa ata ggc aga gcg aca agt gag aat att cca gaa gaa gag     1709
Phe Tyr Glu Ile Gly Arg Ala Thr Ser Glu Asn Ile Pro Glu Glu Glu
    505                 510                 515 gtt ctc aag gga gag ctc gct ggc ata cta ttg gct gaa gga acg ctc     1757
Val Leu Lys Gly Glu Leu Ala Gly Ile Leu Leu Ala Glu Gly Thr Leu
520                 525                 530 ttg agg aaa gac gtt gaa tac ttt gat tca tcc cgc aaa aaa cgg agg     1805
Leu Arg Lys Asp Val Glu Tyr Phe Asp Ser Ser Arg Lys Lys Arg Arg
```

-continued

```
              535                 540                 545                 550 att tca cac cag tat cgt gtt gag ata acc att ggg aaa gac gag gag          1853
Ile Ser His Gln Tyr Arg Val Glu Ile Thr Ile Gly Lys Asp Glu Glu
                555                 560                 565 gag ttt agg gat cgt atc aca tac att ttt gag cgt ttg ttt ggg att          1901
Glu Phe Arg Asp Arg Ile Thr Tyr Ile Phe Glu Arg Leu Phe Gly Ile
        570                 575                 580 act cca agc atc tcg gag aag aaa gga act aac gca gta aca ctc aaa          1949
Thr Pro Ser Ile Ser Glu Lys Lys Gly Thr Asn Ala Val Thr Leu Lys
                585                 590                 595 gtt gcg aag aag aat gtt tat ctt aaa gtc aag gaa att atg gac aac          1997
Val Ala Lys Lys Asn Val Tyr Leu Lys Val Lys Glu Ile Met Asp Asn
        600                 605                 610 ata gag tcc cta cat gcc ccc tcg gtt ctc agg gga ttc ttc gaa ggc          2045
Ile Glu Ser Leu His Ala Pro Ser Val Leu Arg Gly Phe Phe Glu Gly
615                 620                 625                 630 gac ggt tca gta aac agg gtt agg agg agt att gtt gca acc cag ggt          2093
Asp Gly Ser Val Asn Arg Val Arg Arg Ser Ile Val Ala Thr Gln Gly
                635                 640                 645 aca aag aac gag tgg aag att aaa ctg gtg tca aaa ctg ctc tcc cag          2141
Thr Lys Asn Glu Trp Lys Ile Lys Leu Val Ser Lys Leu Leu Ser Gln
        650                 655                 660 ctt ggt atc cct cat caa acg tac acg tat cag tat cag gaa aat ggg          2189
Leu Gly Ile Pro His Gln Thr Tyr Thr Tyr Gln Tyr Gln Glu Asn Gly
                665                 670                 675 aaa gat cgg agc agg tat ata ctg gag ata act gga aag gac gga ttg          2237
Lys Asp Arg Ser Arg Tyr Ile Leu Glu Ile Thr Gly Lys Asp Gly Leu
        680                 685                 690 ata ctg ttc caa aca ctc att gga ttc atc agt gaa aga aag aac gct          2285
Ile Leu Phe Gln Thr Leu Ile Gly Phe Ile Ser Glu Arg Lys Asn Ala
695                 700                 705                 710 ctg ctt aat aag gca ata tct cag agg gaa atg aac aac ttg gaa aac          2333
Leu Leu Asn Lys Ala Ile Ser Gln Arg Glu Met Asn Asn Leu Glu Asn
                715                 720                 725 aat gga ttt tac agg ctc agt gaa ttc aat gtc agc acg gaa tac tat          2381
Asn Gly Phe Tyr Arg Leu Ser Glu Phe Asn Val Ser Thr Glu Tyr Tyr
        730                 735                 740 gag ggc aag gtc tat gac tta act ctt gaa gga act ccc tac tac ttt          2429
Glu Gly Lys Val Tyr Asp Leu Thr Leu Glu Gly Thr Pro Tyr Tyr Phe
                745                 750                 755 gcc aat ggc ata ttg acc cat aac tcc ctg tac ccc tca atc atc atc          2477
Ala Asn Gly Ile Leu Thr His Asn Ser Leu Tyr Pro Ser Ile Ile Ile
        760                 765                 770 acc cac aac gtc tcg ccg gat acg ctc aac aga gaa gga tgc aag gaa          2525
Thr His Asn Val Ser Pro Asp Thr Leu Asn Arg Glu Gly Cys Lys Glu
775                 780                 785                 790 tat gac gtt gcc cca cag gtc ggc cac cgc ttc tgc aag gac ttc cca          2573
Tyr Asp Val Ala Pro Gln Val Gly His Arg Phe Cys Lys Asp Phe Pro
                795                 800                 805 gga ttt atc ccg agc ctg ctt gga gac ctc cta gag gag agg cag aag          2621
Gly Phe Ile Pro Ser Leu Leu Gly Asp Leu Leu Glu Glu Arg Gln Lys
        810                 815                 820 ata aag aag aag atg aag gcc acg att gac ccg atc gag agg aag ctc          2669
Ile Lys Lys Lys Met Lys Ala Thr Ile Asp Pro Ile Glu Arg Lys Leu
                825                 830                 835 ctc gat tac agg cag agg gcc atc aag atc ctg gca aac agc atc cta          2717
Leu Asp Tyr Arg Gln Arg Ala Ile Lys Ile Leu Ala Asn Ser Ile Leu
        840                 845                 850 ccc gag gaa tgg ctt cca gtc ctc gag gaa ggg gag gtt cac ttc gtc          2765
```

```
Pro Glu Glu Trp Leu Pro Val Leu Glu Glu Gly Val His Phe Val
855                 860                 865                 870 agg att gga gag ctc ata gac cgg atg atg gag gaa aat gct ggg aaa      2813
Arg Ile Gly Glu Leu Ile Asp Arg Met Met Glu Glu Asn Ala Gly Lys
            875                 880                 885 gta aag aga gag ggc gag acg gaa gtg ctt gag gtc agt ggg ctt gaa      2861
Val Lys Arg Glu Gly Glu Thr Glu Val Leu Glu Val Ser Gly Leu Glu
            890                 895                 900 gtc ccg tcc ttt aac agg aga act aac aag gcc gag ctc aag aga gta      2909
Val Pro Ser Phe Asn Arg Arg Thr Asn Lys Ala Glu Leu Lys Arg Val
            905                 910                 915 aag gcc ctg att agg cac gat tat tct ggc aag gtc tac acc atc aga      2957
Lys Ala Leu Ile Arg His Asp Tyr Ser Gly Lys Val Tyr Thr Ile Arg
            920                 925                 930 ctg aag tcg ggg agg aga ata aag ata acc tct ggc cac agc ctc ttc      3005
Leu Lys Ser Gly Arg Arg Ile Lys Ile Thr Ser Gly His Ser Leu Phe
935                 940                 945                 950 tct gtg aga aac ggg gag ctc gtt gaa gtt acg ggc gat gaa cta aag      3053
Ser Val Arg Asn Gly Glu Leu Val Glu Val Thr Gly Asp Glu Leu Lys
            955                 960                 965 cca ggt gac ctc gtt gca gtc ccg cgg aga ttg gag ctt cct gag aga      3101
Pro Gly Asp Leu Val Ala Val Pro Arg Arg Leu Glu Leu Pro Glu Arg
            970                 975                 980 aac cac gtg ctg aac ctc gtt gaa ctg ctc ctt gga acg cca gaa gaa      3149
Asn His Val Leu Asn Leu Val Glu Leu Leu Leu Gly Thr Pro Glu Glu
            985                 990                 995 gaa act ttg gac atc gtc atg acg atc cca gtc aag ggt aag aag aac      3197
Glu Thr Leu Asp Ile Val Met Thr Ile Pro Val Lys Gly Lys Lys Asn
    1000                1005                1010 ttc ttt aaa ggg atg ctc agg act ttg cgc tgg att ttc gga gag gaa      3245
Phe Phe Lys Gly Met Leu Arg Thr Leu Arg Trp Ile Phe Gly Glu Glu
1015                1020                1025                1030 aag agg ccc aga acc gcg aga cgc tat ctc agg cac ctt gag gat ctg      3293
Lys Arg Pro Arg Thr Ala Arg Arg Tyr Leu Arg His Leu Glu Asp Leu
            1035                1040                1045 ggc tat gtc cgg ctt aag aag atc ggc tac gaa gtc ctc gac tgg gac      3341
Gly Tyr Val Arg Leu Lys Lys Ile Gly Tyr Glu Val Leu Asp Trp Asp
            1050                1055                1060 tca ctt aag aac tac aga agg ctc tac gag gcg ctt gtc gag aac gtc      3389
Ser Leu Lys Asn Tyr Arg Arg Leu Tyr Glu Ala Leu Val Glu Asn Val
    1065                1070                1075 aga tac aac ggc aac aag agg gag tac ctc gtt gaa ttc aat tcc atc      3437
Arg Tyr Asn Gly Asn Lys Arg Glu Tyr Leu Val Glu Phe Asn Ser Ile
    1080                1085                1090 cgg gat gca gtt ggc ata atg ccc cta aaa gag ctg aag gag tgg aag      3485
Arg Asp Ala Val Gly Ile Met Pro Leu Lys Glu Leu Lys Glu Trp Lys
1095                1100                1105                1110 atc ggc acg ctg aac ggc ttc aga atg aga aag ctc att gaa gtg gac      3533
Ile Gly Thr Leu Asn Gly Phe Arg Met Arg Lys Leu Ile Glu Val Asp
            1115                1120                1125 gag tcg tta gca aag ctc ctc ggc tac tac gtg agc gag ggc tat gca      3581
Glu Ser Leu Ala Lys Leu Leu Gly Tyr Tyr Val Ser Glu Gly Tyr Ala
            1130                1135                1140 aga aag cag agg aat ccc aaa aac ggc tgg agc tac agc gtg aag ctc      3629
Arg Lys Gln Arg Asn Pro Lys Asn Gly Trp Ser Tyr Ser Val Lys Leu
            1145                1150                1155 tac aac gaa gac cct gaa gtg ctg gac gat atg gag aga ctc gcc agc      3677
Tyr Asn Glu Asp Pro Glu Val Leu Asp Asp Met Glu Arg Leu Ala Ser
    1160                1165                1170
```

| | |
|---|---|
| agg ttt ttc ggg aag gtg agg cgg ggc agg aac tac gtt gag ata ccg<br>Arg Phe Phe Gly Lys Val Arg Arg Gly Arg Asn Tyr Val Glu Ile Pro<br>1175                     1180                     1185                     1190 | 3725 |
| aag aag atc ggc tac ctg ctc ttt gag aac atg tgc ggt gtc cta gcg<br>Lys Lys Ile Gly Tyr Leu Leu Phe Glu Asn Met Cys Gly Val Leu Ala<br>             1195                     1200                     1205 | 3773 |
| gag aac aag agg att ccc gag ttc gtc ttc acg tcc ccg aaa ggg gtt<br>Glu Asn Lys Arg Ile Pro Glu Phe Val Phe Thr Ser Pro Lys Gly Val<br>1210                     1215                     1220 | 3821 |
| cgg ctg gcc ttc ctt gag ggg tac tca tcg gcg atg gcg acg tcc acc<br>Arg Leu Ala Phe Leu Glu Gly Tyr Ser Ser Ala Met Ala Thr Ser Thr<br>             1225                     1230                     1235 | 3869 |
| gaa caa gag act cag gct ctc aac gaa aag cga gct tta gcg aac cag<br>Glu Gln Glu Thr Gln Ala Leu Asn Glu Lys Arg Ala Leu Ala Asn Gln<br>1240                     1245                     1250 | 3917 |
| ctc gtc ctc ctc ttg aac tcg gtg ggg gtc tct gct gta aaa ctt ggg<br>Leu Val Leu Leu Leu Asn Ser Val Gly Val Ser Ala Val Lys Leu Gly<br>1255                     1260                     1265                     1270 | 3965 |
| cac gac agc ggc gtt tac agg gtc tat ata aac gag gag ctc ccg ttc<br>His Asp Ser Gly Val Tyr Arg Val Tyr Ile Asn Glu Glu Leu Pro Phe<br>             1275                     1280                     1285 | 4013 |
| gta aag ctg gac aag aaa aag aac gcc tac tac tca cac gtg atc ccc<br>Val Lys Leu Asp Lys Lys Lys Asn Ala Tyr Tyr Ser His Val Ile Pro<br>1290                     1295                     1300 | 4061 |
| aag gaa gtc ctg agc gag gtc ttt ggg aag gtt ttc cag aaa aac gtc<br>Lys Glu Val Leu Ser Glu Val Phe Gly Lys Val Phe Gln Lys Asn Val<br>1305                     1310                     1315 | 4109 |
| agt cct cag acc ttc agg aag atg gtc gag gac gga aga ctc gat ccc<br>Ser Pro Gln Thr Phe Arg Lys Met Val Glu Asp Gly Arg Leu Asp Pro<br>1320                     1325                     1330 | 4157 |
| gaa aag gcc cag agg ctc tcc tgg ctc att gag ggg gac gta gtg ctc<br>Glu Lys Ala Gln Arg Leu Ser Trp Leu Ile Glu Gly Asp Val Val Leu<br>1335                     1340                     1345                     1350 | 4205 |
| gac cgc gtt gag tcc gtt gat gtg gaa gac tac gat ggt tat gtc tat<br>Asp Arg Val Glu Ser Val Asp Val Glu Asp Tyr Asp Gly Tyr Val Tyr<br>             1355                     1360                     1365 | 4253 |
| gac ctg agc gtc gag gac aac gag aac ttc ctc gtt ggc ttt ggg ttg<br>Asp Leu Ser Val Glu Asp Asn Glu Asn Phe Leu Val Gly Phe Gly Leu<br>1370                     1375                     1380 | 4301 |
| gtc tat gct cac aac agc tac tac ggt tac tac ggc tat gca agg gcg<br>Val Tyr Ala His Asn Ser Tyr Tyr Gly Tyr Tyr Gly Tyr Ala Arg Ala<br>1385                     1390                     1395 | 4349 |
| cgc tgg tac tgc aag gag tgt gca gag agc gta acg gcc tgg gga agg<br>Arg Trp Tyr Cys Lys Glu Cys Ala Glu Ser Val Thr Ala Trp Gly Arg<br>1400                     1405                     1410 | 4397 |
| gag tac ata acg atg acc atc aag gag ata gag gaa aag tac ggc ttt<br>Glu Tyr Ile Thr Met Thr Ile Lys Glu Ile Glu Glu Lys Tyr Gly Phe<br>1415                     1420                     1425                     1430 | 4445 |
| aag gta atc tac agc gac acc gac gga ttt ttt gcc aca ata cct gga<br>Lys Val Ile Tyr Ser Asp Thr Asp Gly Phe Phe Ala Thr Ile Pro Gly<br>             1435                     1440                     1445 | 4493 |
| gcc gat gct gaa acc gtc aaa aag aag gct atg gag ttc ctc aag tat<br>Ala Asp Ala Glu Thr Val Lys Lys Lys Ala Met Glu Phe Leu Lys Tyr<br>1450                     1455                     1460 | 4541 |
| atc aac gcc aaa ctt ccg ggc gcg ctt gag ctc gag tac gag ggc ttc<br>Ile Asn Ala Lys Leu Pro Gly Ala Leu Glu Leu Glu Tyr Glu Gly Phe<br>1465                     1470                     1475 | 4589 |
| tac aaa cgc ggc ttc ttc gtc acg aag aag aag tat gcg gtg ata gac<br>Tyr Lys Arg Gly Phe Phe Val Thr Lys Lys Lys Tyr Ala Val Ile Asp<br>1480                     1485                     1490 | 4637 |

-continued

```
gag gaa ggc aag ata aca acg cgc gga ctt gag att gtg agg cgt gac      4685
Glu Glu Gly Lys Ile Thr Thr Arg Gly Leu Glu Ile Val Arg Arg Asp
1495                1500                1505                1510 tgg agc gag ata gcg aaa gag acg cag gcg agg gtt ctt gaa gct ttg      4733
Trp Ser Glu Ile Ala Lys Glu Thr Gln Ala Arg Val Leu Glu Ala Leu
            1515                1520                1525 cta aag gac ggt gac gtc gag aag gcc gtg agg ata gtc aaa gaa gtt      4781
Leu Lys Asp Gly Asp Val Glu Lys Ala Val Arg Ile Val Lys Glu Val
        1530                1535                1540 acc gaa aag ctg agc aag tac gag gtt ccg ccg gag aag ctg gtg atc      4829
Thr Glu Lys Leu Ser Lys Tyr Glu Val Pro Pro Glu Lys Leu Val Ile
    1545                1550                1555 cac gag cag ata acg agg gat tta aag gac tac aag gca acc ggt ccc      4877
His Glu Gln Ile Thr Arg Asp Leu Lys Asp Tyr Lys Ala Thr Gly Pro
1560                1565                1570 cac gtt gcc gtt gcc aag agg ttg gcc gcg aga gga gtc aaa ata cgc      4925
His Val Ala Val Ala Lys Arg Leu Ala Ala Arg Gly Val Lys Ile Arg
1575                1580                1585                1590 cct gga acg gtg ata agc tac atc gtg ctc aag ggc tct ggg agg ata      4973
Pro Gly Thr Val Ile Ser Tyr Ile Val Leu Lys Gly Ser Gly Arg Ile
            1595                1600                1605 ggc gac agg gcg ata ccg ttc gac gag ttc gac ccg acg aag cac aag      5021
Gly Asp Arg Ala Ile Pro Phe Asp Glu Phe Asp Pro Thr Lys His Lys
        1610                1615                1620 tac gac gcc gag tac tac att gag aac cag gtt ctc cca gcc gtt gag      5069
Tyr Asp Ala Glu Tyr Tyr Ile Glu Asn Gln Val Leu Pro Ala Val Glu
    1625                1630                1635 aga att ctg aga gcc ttc ggt tac cgc aag gaa gac ctg cgc tac cag      5117
Arg Ile Leu Arg Ala Phe Gly Tyr Arg Lys Glu Asp Leu Arg Tyr Gln
1640                1645                1650 aag acg aga cag gtt ggt ttg agt gct tgg ctg aag ccg aag gga act      5165
Lys Thr Arg Gln Val Gly Leu Ser Ala Trp Leu Lys Pro Lys Gly Thr
1655                1660                1665                1670 tgacctttcc atttgttttc cagcggataa ccctttaact tccctttcaa aaactcccct      5225
tagggaaaga ccatgaagat agaaatccgg cggcgcccgg ttaaatacgc taggatagaa      5285
gtgaagccag acggcagggt agtcgtcact gccccgaggg ttcaacgttg agaagtt        5342

<210> SEQ ID NO 2
<211> LENGTH: 774
<212> TYPE: PRT
<213> ORGANISM: Pyrococcus kodakaraensis

<400> SEQUENCE: 2

Met Ile Leu Asp Thr Asp Tyr Ile Thr Glu Asp Gly Lys Pro Val Ile
 1               5                  10                  15

Arg Ile Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Glu Val Lys Lys Ile Thr Ala Glu Arg His Gly Thr Val Val Thr
        50                  55                  60

Val Lys Arg Val Glu Lys Val Gln Lys Lys Phe Leu Gly Arg Pro Val
 65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110
```

```
Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525
```

| | | | | | | | | | | | | |
|---|---|---|---|---|---|---|---|---|---|---|---|---|
|Glu|Glu|Lys|Tyr|Gly|Phe|Lys|Val|Ile|Tyr|Ser|Asp|Thr|Asp|Gly|Phe|
| | |530| | |535| | |540| | | |

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770

<210> SEQ ID NO 3
<211> LENGTH: 2325
<212> TYPE: DNA
<213> ORGANISM: Pyrococcus kodakaraensis

<400> SEQUENCE: 3

```
atgatcctcg acactgacta cataaccgag gatggaaagc tgtcataag aattttcaag      60 aaggaaaacg gcgagtttaa gattgagtac gaccggactt ttgaacccta cttctacgcc    120
ctcctgaagg acgattctgc cattgaggaa gtcaagaaga taaccgccga gaggcacggg    180
acggttgtaa cggttaagcg ggttgaaaag gttcagaaga gttcctcgg gagaccagtt    240 gaggtctgga aactctactt tactcatccg caggacgtcc cagcgataag ggacaagata    300
cgagagcatc cagcagttat tgacatctac gagtacgaca taccettcgc caagcgctac    360 ctcatagaca agggattagt gccaatggaa ggcgacgagg agctgaaaat gctcgccttc    420
gacattgaaa ctctctacca tgagggcgag gagttcgccg aggggccaat ccttatgata    480
agctacgccg acgaggaagg ggccagggta taacttgga agaacgtgga tctcccctac    540
gttgacgtcg tctcgacgga gagggagatg ataaagcgct tcctccgtgt tgtgaaggag    600
aaagacccgg acgttctcat aacctacaac ggcgacaact tcgacttcgc ctatctgaaa    660
aagcgctgtg aaaagctcgg aataaacttc gccctcggaa gggatggaag cgagccgaag    720
```

```
attcagagga tgggcgacag gtttgccgtc gaagtgaagg gacgatacac cttcgatctc    780
tatcctgtga taagacggac gataaacctg cccacataca cgcttgaggc cgtttatgaa    840
gccgtcttcg gtcagccgaa ggagaaggtt tacgctgagg aaataaccac agcctgggaa    900
accggcgaga accttgagag agtcgcccgc tactcgatgg aagatgcgaa ggtcacatac    960
gagcttggga aggagttcct tccgatggag gcccagcttt ctcgcttaat cggccagtcc   1020
ctctgggacg tctcccgctc cagcactggc aacctcgttg agtggttcct cctcaggaag   1080
gcctatgaga ggaatgagct ggccccgaac aagcccgatg aaaaggagct ggccagaaga   1140
cggcagagct atgaaggagg ctatgtaaaa gagcccgaga gagggttgtg ggagaacata   1200
gtgtacctag attttagatc cctgtacccc tcaatcatca tcacccacaa cgtctcgccg   1260
gatacgctca acagagaagg atgcaaggaa tatgacgttg ccccacaggt cggccaccgc   1320
ttctgcaagg acttcccagg atttatcccg agcctgcttg agacctcct agaggagagg    1380 cagaagataa agaagaagat gaaggccacg attgacccga tcgagaggaa gctcctcgat   1440
tacaggcaga gggccatcaa gatcctggca aacagctact acggttacta cggctatgca   1500
agggcgcgct ggtactgcaa ggagtgtgca gagagcgtaa cggcctgggg aagggagtac   1560
ataacgatga ccatcaagga gatagaggaa aagtacggct ttaaggtaat ctacagcgac   1620
accgacggat tttttgccac aatacctgga gccgatgctg aaaccgtcaa aaagaaggct   1680
atggagttcc tcaagtatat caacgccaaa cttccgggcg cgcttgagct cgagtacgag   1740
ggcttctaca acgcggctt cttcgtcacg aagaagaagt atgcggtgat agacgaggaa   1800
ggcaagataa caacgcgcgg acttgagatt gtgaggcgtg actggagcga gatagcgaaa   1860
gagacgcagg cgagggttct tgaagctttg ctaaaggacg gtgacgtcga gaaggccgtg   1920
aggatagtca agaagttac cgaaaagctg agcaagtacg aggttccgcc ggagaagctg    1980
gtgatccacg agcagataac gagggattta aaggactaca aggcaaccgg tccccacgtt   2040
gccgttgcca agaggttggc cgcgagagga gtcaaaatac gccctggaac ggtgataagc   2100
tacatcgtgc tcaagggctc tgggaggata ggcgacaggg cgataccgtt cgacgagttc   2160
gacccgacga agcacaagta cgacgccgag tactacattg agaaccaggt tctcccagcc   2220
gttgagagaa ttctgagagc cttcggttac cgcaaggaag acctgcgcta ccagaagacg   2280
agacaggttg gtttgagtgc ttggctgaag ccgaagggaa cttga             2325

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 4
gaaactctct acgaggaggg cgaggagttc gccg                                34

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 5
cggcgaactc ctcgccctcc tcgtagagag tttc                                34
```

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 6
gaaactctct acgacgaggg cgaggagttc gccg                                34

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 7
cggcgaactc ctcgccctcg tcgtagagag tttc                                34

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 8
gaaactctct actacgaggg cgaggagttc gccg                                34

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 9
cggcgaactc ctcgccctcg tagtagagag tttc                                34

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 10
gaaactctct acgccgaggg cgaggagttc gc                                  32

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 11
gcgaactcct cgccctcggc gtagagagtt tc                                  32

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 12
gaaactctct acaaggaggg cgaggagttc                                          30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 13
gaactcctcg ccctccttgt agagagtttc                                          30

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 14
aaagctctct acagggaggg cgaggagttc gc                                       32

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 15
gcgaactcct cgccctccct gtagagagtt tc                                       32

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 16
gaaactctct actctgaggg cgaggagttc gccg                                     34

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 17
cggcgaactc ctcgccctca gagtagagag tttc                                     34

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 18
gaaactctct accaggaggg cgaggagttc gccg                                     34

<210> SEQ ID NO 19

-continued

```
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 19
cggcgaactc ctcgccctcc tggtagagag tttc                                34

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 20
ggtgttccct tgatgtagca ca                                             22

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 21
acatgtattt gcatggaaaa caactc                                         26

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 22
agtgcttcgt gcccgatgac                                                20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 23
tgccccttgg tgacatactc g                                              21

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence:primer

<400> SEQUENCE: 24
aaaaacgcgt caccagtcac agaaaagcat cttac                               35

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 25
```

```
aaaaacgcgt caaccaagtc attctgagaa tagt                                    34

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 26
ggattagtat agtgccaatg gssggcga                                           28

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 27
gagggcagaa gtttattccg agctt                                              25

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 28
cgccagggtt ttcccagtca cgac                                               24
```